US006417173B1

(12) United States Patent
Roufa et al.

(10) Patent No.: US 6,417,173 B1
(45) Date of Patent: Jul. 9, 2002

(54) METHODS AND COMPOSITIONS BASED ON INHIBITION OF CELL INVASION AND FIBROSIS BY ANIONIC POLYMERS

(75) Inventors: Dikla Roufa, St. Louis, MO (US); Adrian Harel, Woodmere; Robert C. A. Frederickson, Bentleyville, both of OH (US); George T. Coker, III, Mountain View, CA (US)

(73) Assignee: Gliatech, Inc., Beachwood, OH (US)

( * ) Notice: Subject to any disclaimer, the term of this patent is extended or adjusted under 35 U.S.C. 154(b) by 0 days.

(21) Appl. No.: 09/476,158

(22) Filed: Dec. 30, 1999

Related U.S. Application Data

(63) Continuation of application No. 09/388,825, filed on Sep. 1, 1999, now Pat. No. 6,127,348, which is a division of application No. 08/469,560, filed on Jun. 6, 1995, now Pat. No. 6,020,326, which is a continuation of application No. 07/708,660, filed on May 31, 1991, now Pat. No. 5,605,938.

(51) Int. Cl.$^7$ ............................................. A61K 31/715

(52) U.S. Cl. ................. 514/54; 514/2; 514/21; 514/59; 424/422; 424/423; 424/424; 424/425; 530/350; 530/356; 530/857; 604/289; 604/290; 604/304; 604/306; 604/307; 623/1; 623/2; 623/11; 623/22

(58) Field of Search ................. 424/422, 423, 424/424, 425; 514/2, 21, 54, 59; 530/350, 356, 857; 604/289, 290, 304, 306, 307; 623/1, 2, 11, 22

(56) References Cited

U.S. PATENT DOCUMENTS

| 4,755,379 A | | 7/1988 | Jozefonvicz et al. |
| 4,803,075 A | | 2/1989 | Wallace et al. |
| 4,886,787 A | | 12/1989 | de Belder et al. |
| 5,015,677 A | | 5/1991 | Benedict et al. |
| 5,166,187 A | | 11/1992 | Collombel et al. |
| 5,459,054 A | | 10/1995 | Skjak-Brack et al. |
| 5,605,938 A | | 2/1997 | Roufa et al. |
| 5,705,177 A | * | 1/1998 | Roufa et al. |
| 5,705,178 A | | 1/1998 | Roufa et al. |
| 5,981,509 A | | 11/1999 | Akima et al. |
| 5,994,325 A | * | 11/1999 | Roufa et al. |
| 6,020,326 A | | 2/2000 | Roufa et al. |
| 6,083,930 A | | 7/2000 | Roufa et al. |
| 6,127,348 A | * | 10/2000 | Roufa et al. |

FOREIGN PATENT DOCUMENTS

| DD | 252 838 A | 12/1987 |
| DD | 252 839 A | 12/1987 |
| DE | 4039867 A1 | 6/1992 |
| JP | 02-1287 | 1/1990 |
| WO | WO 87/05808 | 10/1987 |
| WO | WO 91/06303 | 5/1991 |
| WO | WO 91/16058 | 10/1991 |
| WO | WO 92/19249 | 11/1992 |
| WO | WO 96/05945 | 2/1996 |
| WO | WO 99/00417 | 1/1999 |
| WO | WO 99/40909 | 8/1999 |

OTHER PUBLICATIONS

Balazs & Darzynkiewicz, 1972, The Effect of Hyaluronic Acid on Fibroblasts, Mononuclear Phagocytes and Lymphocytes, in Biology of Gibrblast (Kulonen and Pikkararein, Eds.) Academic Press: London & New York, pp 237–252.

Binor et al., 1984, "The Effect of 32% Dextran 70 (Dex), Dexamethasone (Dec), Promethazine (Pro), and Ibuprofen (Ibu) in Preventing Postoperative Adhesions", Fertil. Steril. 41 (2 Suppl.):48s(Abstr. 110) 40$^{th}$ Ann. Meeting of the American Fertility Society, New Orleans, LA Apr. 2–7.

Dijkstra et al., "The heterogeneity of mononuclear phagocytes in lymphoid organs: distinct macrophage subpopulations in the rat recognized by monoclonal antibodies ED1, ED2, and ED3", Immunology. Mar.;1985 54(3):589–99.

Klebe et al., 1986, "Regulation of cell motility, morphology, and growth by sulfated glycosaminoglycans". Cell Motil Cytoskeleton 6(3):273–81.

Majack & Clowes, 1984, Inhibition of vascular smooth muscle cell migration by heparin–like glycosaminoglycans. J Cell Physiol. 118(3):253–6.

Rosenberg et al., 1986, "Biological roles of dermatan sulphate proteoglycans", Ciba Found Symp. 124:47–68.

Wadstrom T. & Ljungh A., 1999, Glycosaminoglycan–binding Microbial Proteins in Tissue Adhesion and Invasion: Key Events in Microbial Pathogenicity. J Med Microbiol. 48(3):223–33.

(List continued on next page.)

Primary Examiner—James O. Wilson
(74) Attorney, Agent, or Firm—Pennie & Edmonds LLP

(57) ABSTRACT

The present invention relates to the discovery that biocompatible anionic polymers can effectively inhibit fibrosis, scar formation, and surgical adhesions. The invention is predicated on the discovery that anionic polymers effectively inhibit invasion of cells associated with detrimental healing processes, and in particular, that the effectiveness of an anionic polymer at inhibiting cell invasion correlates with the anionic charge density of the polymer. Thus the present invention provides a large number of materials for use in methods of inhibiting fibrosis and fibroblast invasion. Anionic polymers for use in the invention include but are not limited to natural proteoglycans, and the glycosaminoglycan moieties of proteoglycans. Additionally, anionic carbohydrates and other anionic polymers may be used. The anionic polymers dextran sulfate and pentosan polysulfate are preferred. In a more preferred embodiment, dextran sulfate, in which the sulfur content is greater than about 10% by weight, may be used. In a more preferred embodiment, the average molecular weight is about 40,000 to 500,000 Daltons. The present invention provides compositions and methods to inhibit fibrosis and scarring associated with surgery. The invention further provides compositions and methods to inhibit glial cell invasion, detrimental bone growth and neurite outgrowth. In a preferred embodiment, the inhibitory compositions further comprise an adhesive protein.

48 Claims, 13 Drawing Sheets

OTHER PUBLICATIONS

Figure 1:
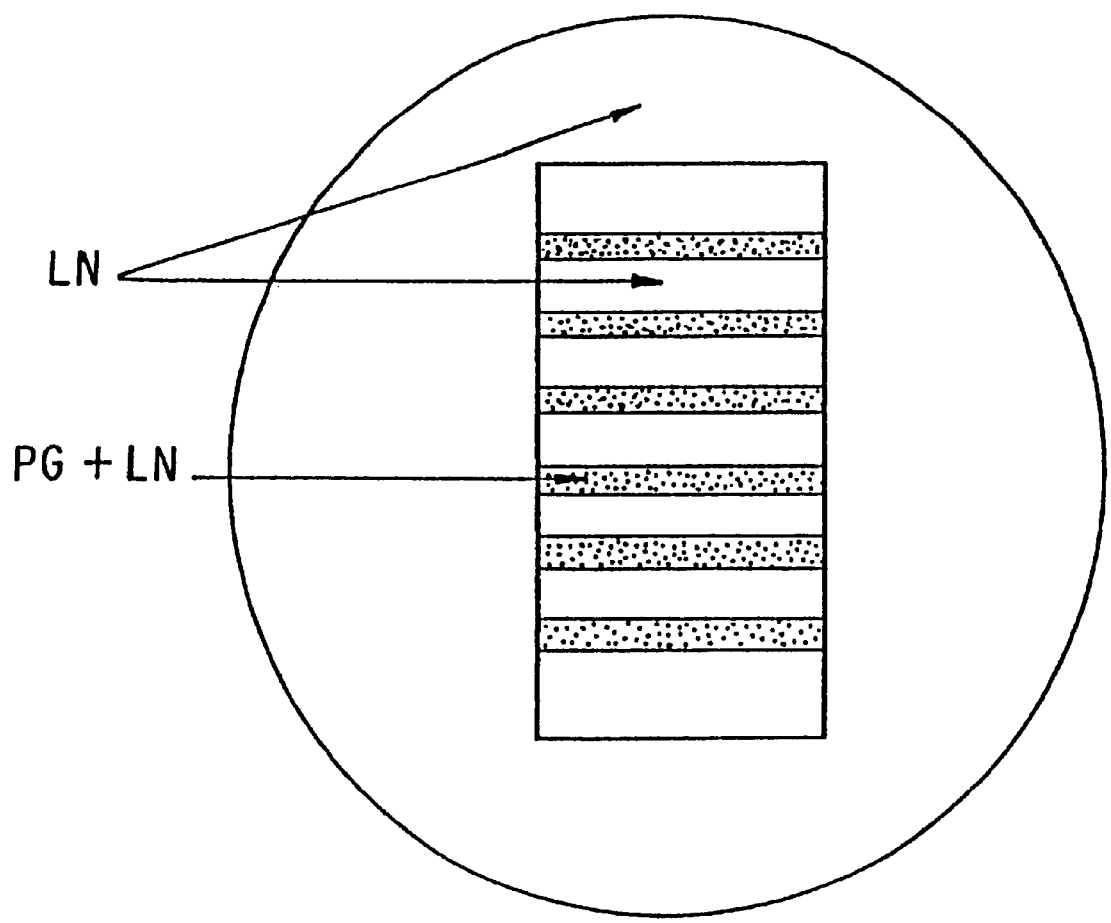
Figure 2A:
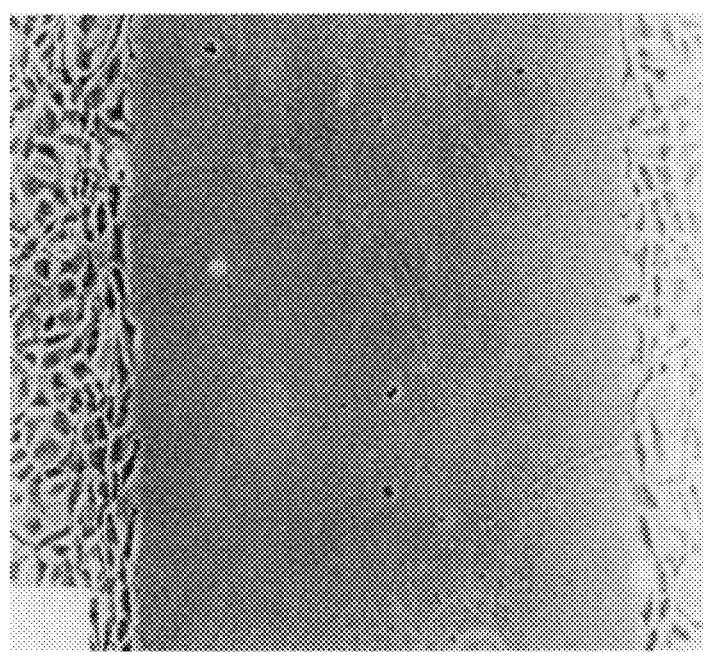
Figure 2B:
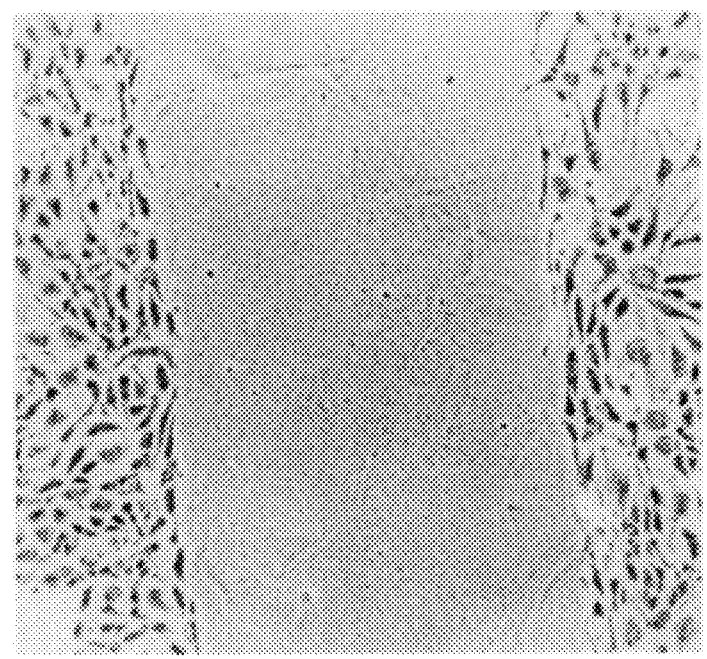
Figure 2C:
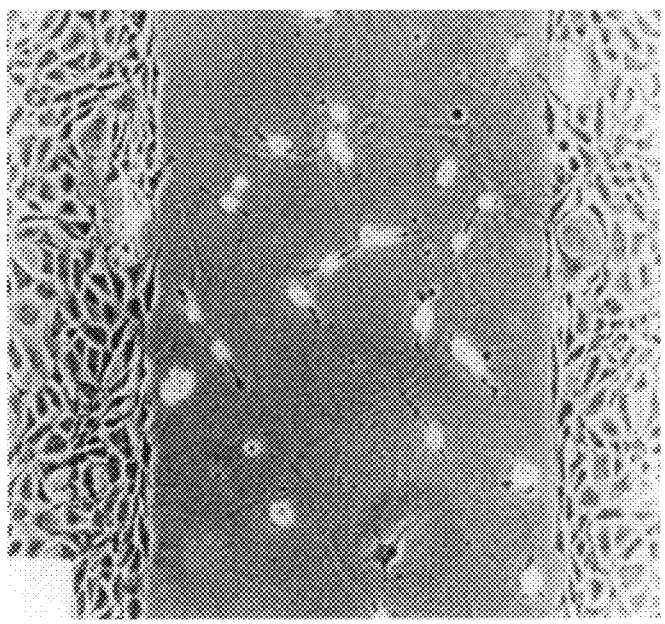
Figure 2D:
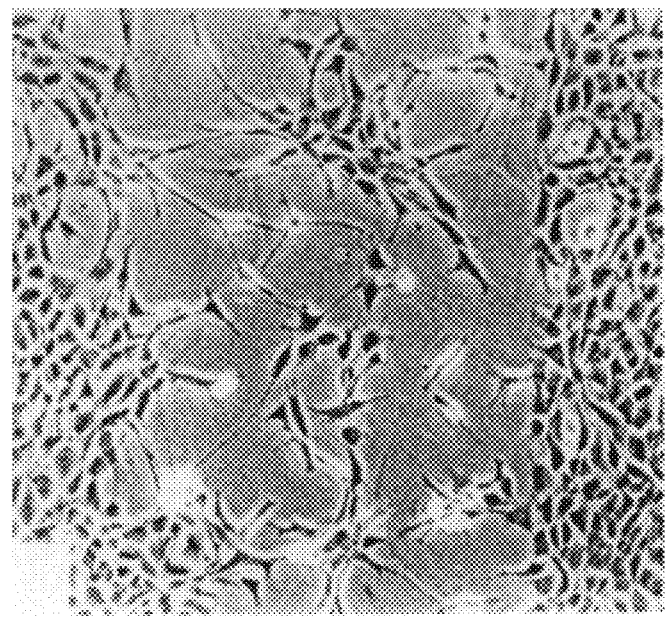

"Haemorrhagic cystitis after radiotherapy," 1987, Lancet 304–306.

Herbert et al., 1988, "Activity of pentosan polysulphate and derived compounds on vascular endothelial cell proliferation and migration induced by acidic and basic FGF in vitro," Biochem. Pharmacol. 37(22): 4281–4288.

Janicki & Sznitowska, 1991, "Effect of ointments for treating scars and keloids on metabolism of collagen in scar and healthy skin," Eur. J. Pharm. 37(3):181–191.

Carbonetto, 1983, "Nerve fiber growth in culture on fibronectin, collagen, and glycosaminoglycan substrates", J. Neuroscience 3(11) 2324–2335.

Kitamura, 1966, "Local hypodermic treatment using sulfalic acid agent", Diagnosis & New Drugs, 3(9) 89–92.

Klauser, 1988, "Induction of fibrinolysis by polyanions in human plasma" Thrombosis and Haemostasis 60(2) 324–327.

Ohno, 1984, "An Experimental Study on Prevention of Radiation–Induced Lung Damage: The Effect of Oral Administration of Dextran Sulphate", Fukuoka Medical Magazine 75(10) 575–593.

Ohno et al., 1978, "Effects of dextran sulfate on pulmonary radiation injury. Clinical and experimental studies", J. Region Disease Soc. Japan 16(10) 756–64.

Oleson, 1959, "Effect of Acid Polysaccharides on the Fibronolytic System in Guinea–Pig Serum", Acta Pharmacologica et Toxicologica 15 307–318.

Quteish et al., 1991, "Light and electron microscopic evaluation of biocompatibility, resorption and penetration characteristics of human collagen graft material", J. Clinical Peridontology 18(5)305–311.

Robertson & Goldstein, 1988, "Heparin inhibits the growth of astrocytes in vitro", Brain Research 447(2) 341–345.

Snow et al., 1990, "Sulfated proteoglycans in astroglial barriers inhibit neurite outgrowth in vitro", Experimental Neurology 114(2) 111–130.

Songer et al., 1990, "Effects of Sodium Hyaluronate on Peridural Fibrosis After Lumbar Laminectomy and Discectomy", Spine 15(6) 550–554.

Stiver et al., 1988, "Inhibition of polymorphonuclear leukocyte chemotaxis by the mucoid exopolysaccharide of Pseudomonas Aeruginosa", Clin. Invest. Med. 11(4) 247–252.

Turck et al., 1987, "Immunological Mediators of Wound Healing and Fibrosis", J. of Cell. Physiol. 5:89–93.

Wujek et al., 1991, "A Carbohydrate Polymer that Effectively Prevents Epidural Fibrosis at Laminectomy Sites in the Rat", Experimental Neurology 114(2) 237–245.

Yamamoto & Hirano, 1979, Clinics with Dextran Sulfate, "The Influence of Dextran Sulfate on Fibrogenesis" pp. 227–238, Tokyo, Iji Publishers.

* cited by examiner-

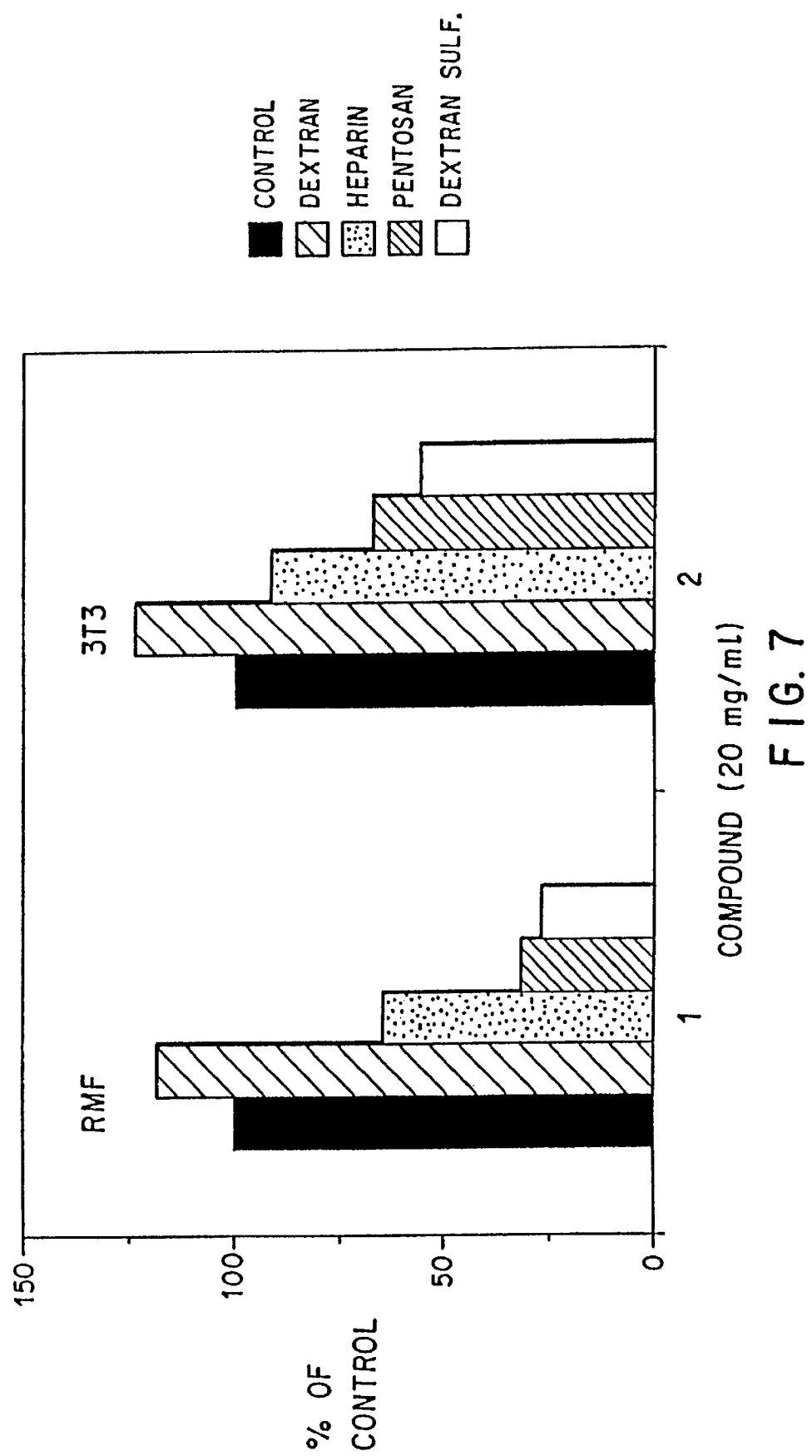

METHODS AND COMPOSITIONS BASED ON INHIBITION OF CELL INVASION AND FIBROSIS BY ANIONIC POLYMERS

This is a continuation of application Ser. No. 09/388,825, filed Sep. 1, 1999, now U.S. Pat. No. 6,127,348, which is a division of application Ser. No. 08/469,560, filed Jun. 6, 1995, now U.S. Pat. No. 6,020,326 which is a continuation of application Ser. No. 07/708,660, filed May 31, 1991, now U.S. Pat. No. 5,605,938, each of which is incorporated by reference herein in its entirety.

1. FIELD OF THE INVENTION

The present invention is directed to compositions comprising biocompatible anionic polymers and methods using such compositions to inhibit fibrosis, and attendant complications such as scar formation and surgical adhesions. Compositions and methods to inhibit glial cell invasion, neurite outgrowth and bone growth are also provided.

2. BACKGROUND OF THE INVENTION

Surgical adhesions—attachment of organs or tissues to each other through scar tissue—can produce clinical problems. The formation of scar tissue is a normal sequel to surgery or other tissue injury and is required for proper wound healing. In some cases, however, the scar tissue overgrows the intended region and creates surgical adhesions. These scar tissue surgical adhesions restrict the normal mobility and function of affected body parts. Where peripheral nerves are involved, fibrous adhesions can elicit severe pain during normal movement. Furthermore scars and keloid tissue (raised scar tissue) are often unsightly and present psychological and emotional problems.

2.1. Peridural Fibrosis

A clinically important example of detrimental scar formation occurs with peridural fibrosis. This condition leads to recurrent low back pain after lumbar laminectomy and diskectomy (Cauchoix et al., 1978, Spine 3:256–259; Jackson, 1971, J. Bone Joint Surg. 53B:409–616; Pheasant, 1985, Orthop. Clin. North Am. 6:319–329; Yong-Hing et al., 1980, Spine 5:59–64). Tissue scar formation restricts nerve root mobility and has been correlated with recurrent radicular pain, often in the same distribution as the previously herniated disk (Benoist, M. et al., 1980, Spine 5:432–436).

2.2. Prevention of Detrimental Scarring

A number of workers have studied the effectiveness of various treatments for preventing peridural fibrosis. Fat grafts have been used with some success to prevent or ameliorate scar formation (LaRocca and Macnab, 1974, J. Bone Joint Surg. 56B:545–550; Langenskold and Kivilvoto, 1976, Clin. Orthop. 115:82–85; Gill et al., 1985, Spine 10:662–667; Gill et al., 1979, Spine 4:176–185; Yong-Hing et al., 1980, Spine 5:59–64). Gelfoam (denatured collagen gel) and silastic membranes showed some effectiveness in preventing adhesions (LaRocca and Macnab, supra); later studies, however, indicated that gelfoam was ineffective or promoted scar formation (Gill, 1985 supra; Gill, 1979, supra; Yong-Hing, supra). Songer et al. reported that sodium hyaluronate, but not gelfoam or anterior fat grafts, retarded fibrosis and reduced fibroblast invasion in a dog model (1990, Spine 15:550–554).

2.3. Cell Invasion and Attachment

Previous work by Snow et al., (1990, Exp. Neurol. 309: 111–130) demonstrated that keratan sulfate/chrondroitin sulfate-proteoglycan (KS/CS-PG) is inhibitory to neurite outgrowth from embryonic (E-9) chick dorsal root ganglia (DRGs). Neurites either stopped abruptly or turned and travelled along the KS/CS-PG stripe border. This phenomenon was dependent upon the concentration of the proteoglycan, with intermediate concentrations producing intermittent patterns of crossing.

A number of studies have considered the role of proteoglycans in cell attachment. Unfractionated cartilage proteoglycans, and to a lesser extent a purified cartilage component, chondroitin sulfate, were found to inhibit fibroblast binding to collagen and fibronectin in vitro (Rich, et al., 1981, Nature 293:224–226). Dermatan sulfate proteoglycan (DS-PG) was observed to inhibit the attachment and spreading of 3T3 fibroblasts on plasma fibronectin-coated culture substrata (Lewandowska et al., 1987, J. Cell Biol. 105:1443–1454; Rosenberg, L. C. et al., 1986, CIBA Foundation Symposium 124:47–68). Dextran sulfate and high molecular weight heparin decreased the initial rate of attachment of chinese hamster ovary and G-8 mouse myoblast cells to collagen (Klebe, R. J. and P. J. Mock, 1982, J. Cell. Physiol. 112:5–9). Proteoglycan isolated from cartilage, freed from glycoproteins and hyaluronic acid, retards attachment of a variety of cell types, including chick embryo fibroblasts, to tissue culture plastic and collagen (Knox, P. and P. Wells, 1979, J. Cell Sci. 40:77–88). However, the glycosaminogLycans keratan sulfate, chondroitin sulfate and hyaluronic acid showed no inhibition of cell attachment (Knox and Wells, supra).

Glycosaminoglycans (GAGs), principally heparan sulfate and dermatan sulfate, also have been identified as mediators of fibroblast (murine 3T3 cell) attachment to fibronectin (Laterra, et al., 1980, Proc. Natl. Acad. Sci. U.S.A. 77:6662–6666). The presence of fibronectin or hyaluronic acid, or both, in a 3-dimensional type I collagen sponge was found to enhance wound healing in vivo, and to support fibroblast invasion with resulting collagen deposition in vitro (Doillon, C. J. et al., 1987, Biomaterials 8:195–200).

Two glial, two epithelial and one fibroblastic cell line showed comparable or decreased binding to collagen-glycosaminoglycan relative to collagen (Reichard-Brown and Akeson, supra). Hyaluronic acid inhibits aggregation of 3T3 fibroblasts (Underhill, C. and Dorfman, A., 1978, Exp. Cell. Res. 117:155–164), and chondroitin sulfate appears to prevent adhesion of leukocytes to endothelium (Fibbi, G. et al., 1983, Biochem. Biophys. Acta 762:512–518).

Studies of the composition of substratum adhesion sites of fibroblasts indicate that cell-surface proteoglycans, predominantly heparan sulfate proteoglycan, play an important role in close and focal contact adhesions (Culp, L. A. et al., 1986, CIBA Foundation Symposium 124:158–83; Izzard, C. S. et al., 1986, Exp. Cell Res. 165:320–336; Lark, M. W. et al.,. 1985, Fed. Proc. 44:394–403; Rollins, B. J. and L. A. Culp, 1979, Biochem. 18:141–148; Culp, L. A. et al., 1979, J. Supramol. Struct. 11:401–427; Culp, L. A. et al., 1978, J. Cell Biol. 79:788–801; Culp, L. A. and H. Bensusan, 1978, Nature 273:680–682; Cornic, M. et al., 1980, Eur. J. Cell Biol. 22:262). Secreted glycosaminoglycans in the substrate-attached material, rather than fibronectin and collagen, appear to play a rate limiting role in the adhesion process of a skeletal mouse myoblast line (Schubert, D. and M. La Corbiere, 1980, J. Biol. Chem. 255:11564–569). A proteoglycan secreted by rat yolk-sac tumor cells inhibited tumor cell binding to fibronectin and type I collagen, but not type IV collagen, which bound 12 times less proteoglycan than did type I collagen (Brennan., M. J. et al., 1983, Cancer Res. 43:4302–4307).

2.4. Adhesive Proteins

The bioadhesive proteins of mussels, oysters and barnacles adhere to a variety of surfaces underwater with high bonding strength. Other DOPA (3,4-dihydroxyphenylalanine) containing proteins also demonstrate adhesive properties. Brown noted evidence of quinone tanning in structural proteins of invertebrates including the bysses of Mytilus and the egg case of the liver fluke, *Fasciola hepatica* (1950, Nature 165:275). Jensen and Morse characterized the adhesion protein used by the marine worm *Phragmatopoma californica* to construct its protective tube (1988, J. Comp. Physiol. B 158:317–324). As with the Mytilus adhesion protein, DOPA is a major constituent of the Phragmatopoma adhesion protein; lysine, serine, and hydroxyl-containing amino acids were also present (Jensen and Morse, 1988, supra).

Additionally, fibrin adhesives are popular and used in a number of applications (see Strausberg, R. L. and R. P. Link, 1990, Trends Biotech 8:53–57).

3. SUMMARY OF THE INVENTION

The present invention relates to the discovery that certain biocompatible anionic polymers can effectively inhibit scar formation, in particular surgical adhesions, and that these anionic polymers generally inhibit fibrosis. The invention is predicated on the discovery that anionic polymers effectively inhibit invasion of cells associated with detrimental healing processes, i.e., fibrosis, and scarring. In particular, anionic polymers of the present invention, termed inhibitory anionic polymers, are useful to inhibit fibroblast invasion, thus regulating the healing process and preventing fibrosis. The anionic polymers of the present invention also inhibit glial cell invasion, bone growth and neurite outgrowth. The present invention further relates to the discovery that the effectiveness of an anionic polymer at inhibiting cell, e.g., fibroblast, invasion correlates in part with the number of anionic charge groups on the polymer. Thus the present invention provides a large number of materials for use in inhibition of scar formation and fibrosis, and in particular surgical adhesions, and a method to determine the suitability of a given material for use in the invention based in part on its effective anionic charge content.

Anionic polymers for use in the invention include dextran sulfate (DX) and pentosan polysulfate (PS). Additionally, natural proteoglycans, or the glycosaminoglycan moieties of proteoglycans, including dermatan sulfate (DS), chondroitin sulfate (CS), keratan sulfate (KS), heparan sulfate (HS), and heparin (HN) may be used. Alginate (AL) also may be used. At suitable concentration, the foregoing molecules can inhibit fibroblast invasion or migration, even in the presence of suitable migration promoting substrates, such as laminin. In a particular aspect, the present invention is directed to methods of using DX, and molecules and compositions comprising DX, to inhibit, prevent or regulate fibroblast invasion and fibrosis and therapeutically, where the foregoing is desired. The invention is further directed to methods of using one or more of the anionic polymers, and compositions comprising one or more of the anionic polymers, to inhibit fibroblast invasion and fibrosis or monocyte/macrophage invasion and therapeutic uses thereof. Such molecules comprising KS, CS, DS, HS, or HN include but are not limited to the disaccharide, glycosaminoglycan, and proteoglycan structures. In a preferred embodiment, DX may be used in the fibroblast inhibitory compositions and methods of this invention.

The invention further provides additional inhibitory anionic polymers suitable for use in preventing scar formation. In one embodiment, an anionic polymer comprising an acidic sulfate in which sulfur content is greater than about 5% by weight may be used. In a more preferred embodiment, the sulfur content is greater than about 10% by weight.

In another embodiment, the invention is further directed to methods of using an inhibitory anionic polymer, preferably dextran sulfate or pentosan polysulfate, combined with an adhesive protein to inhibit fibroblast invasion and fibrosis, and also to inhibit glial cell invasion, neurite outgrowth, and bone growth. The adhesive proteins are capable of cross-linking to the inhibitory molecule and to an appropriate target. The invention therefore provides methods to anchor an inhibitory anionic polymer at the site where inhibitory or regulatory activity is desired.

In a preferred embodiment, the adhesive protein is activated by chemical or enzymatic oxidation of dihydroxyphenylalanine (DOPA) residues to form quinones, applied to the desired location along with molecules comprising KS, CS, DS, HS, HN, DX, or hyaluronic acid (HA), and allowed to cure. The adhesive proteins include but are not limited to adhesion protein from mussels, oysters, barnacles, *Phragmatopoma californica*, or *Fasciola hepatica*, or fibrin, or any adhesive protein produced recombinantly, by chemical synthesis, or by degradation and repolymerization of a natural adhesive protein.

In a further embodiment, molecules comprising one of the inhibitory anionic polymers may be used with one or more other inhibitory anionic polymers, and an adhesive protein.

The instant invention further provides compositions comprising inhibitory anionic polymers and a suitable pharmaceutical carrier, and methods to administer the compositions to inhibit scar formation, and fibrosis in general, and to inhibit undesired bone growth, invasion of glial cells and/or neurite outgrowth.

The present invention also provides compositions comprising effective amounts of an inhibitory anionic polymer, preferably dextran sulfate or pentosan polysulfate, an effective amount of an adhesive protein, and a pharmaceutically acceptable carrier.

| | |
|---|---|
| AL | alginate |
| CS | chondroitin sulfate |
| DS | dermatan sulfate |
| DX | dextran sulfate |
| GAG | glycosaminoglycan |
| HA | hyaluronic acid |
| HN | heparin |
| HS | heparan sulfate |
| KS | keratan sulfate |
| LN | laminin |
| PG | proteoglycan |
| PS | pentosan polysulfate |

Cell adhesion—the initial interaction between the cell surface and the substratum, which results in attachment and subsequent cell spreading.

Cell migration—cell movement within the same substratum.

Cell invasion—cell movement from one type of substratum to another type of substratum.

4. DESCRIPTION OF THE FIGURES

FIG. 1. Schematic diagram of the stripe assay plate showing alternating bands of laminin (LN) and proteoglycan (PG) plus LN, and an overlay of LN throughout the plate.

FIGS. 2A–2D. Dose dependent effect of DS-PG on 3T3 cell adhesion, migration and invasion. Photomicrographs of live 3T3 cells grown in 60 mm tissue culture dishes coated as described in Section 7.1.2., infra, with alternating bands of LN and DS-PG/LN at various DS-PG concentrations for 3 days. (A) 0.8 mg/ml DS-PG, (B) 0.4 mg/ml DS-PG, (C) 0.2 mg/ml DS-PG, and (D) 0.1 mg/ml DS/PG. (100×)

FIGS. 3A–3D. Time dependent effect of DS-PG on C6 cell adhesion, migration and invasion. Photomicrographs of live C6 cells grown in 60 mm tissue culture dishes coated as described in Section 7.1.2., infra, with alternating bands of LN and DS-PG/LN at 0.8 mg/ml DS-PG for (A) 2 hrs, (B) 1 day, (C) 2 days, and (D) 6 days. Note the stability of the inhibition up to 6 days and the limited cell invasion at day 6. (100×)

Figure 4A:
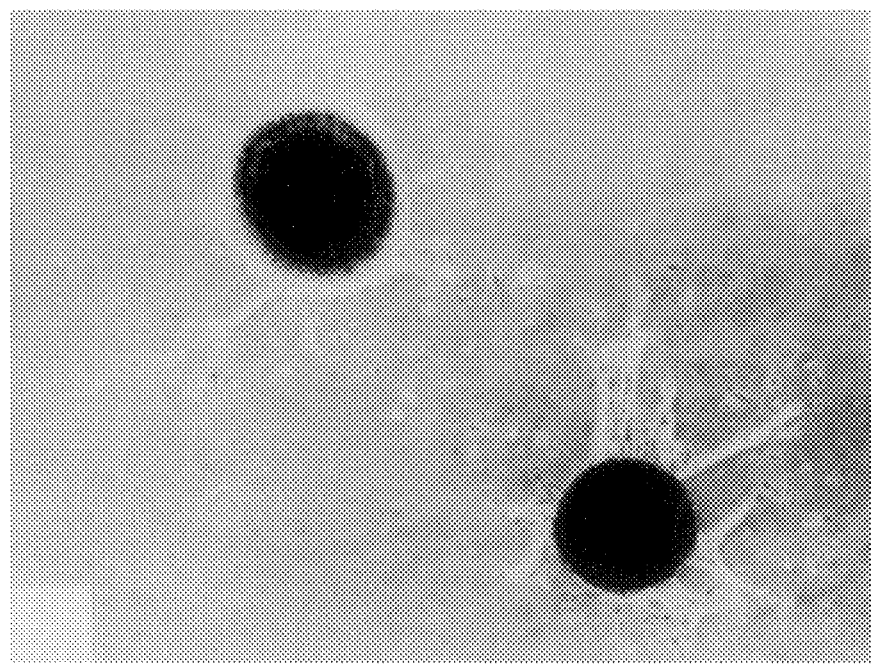
Figure 4B:
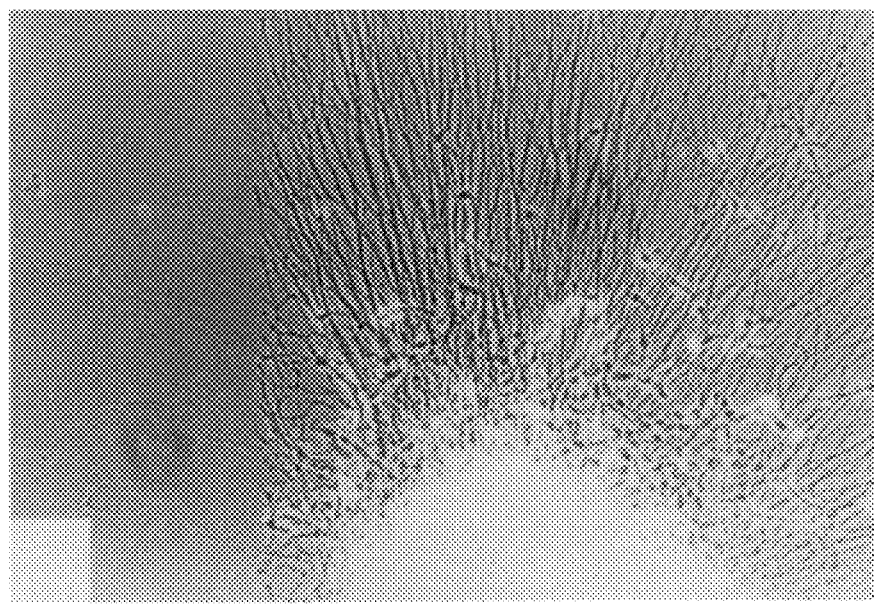
Figure 5A:
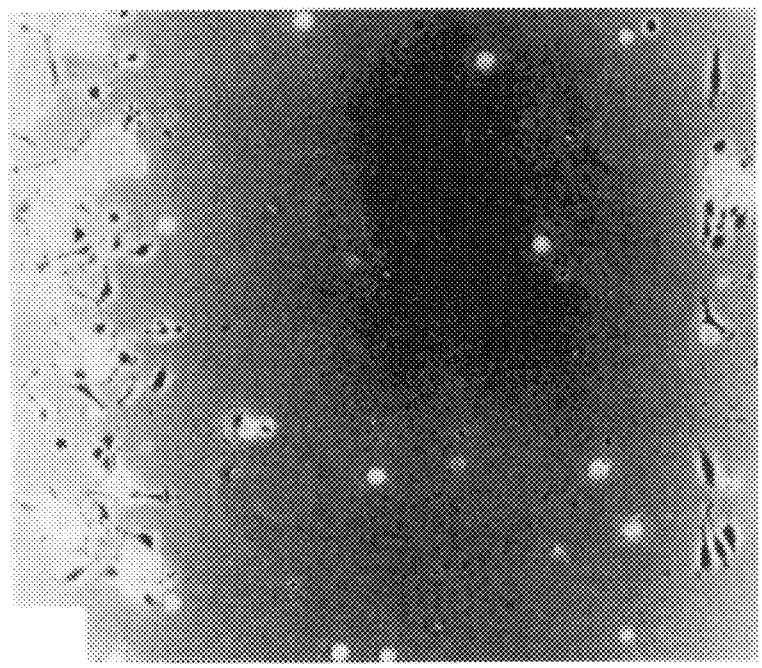
Figure 5B:
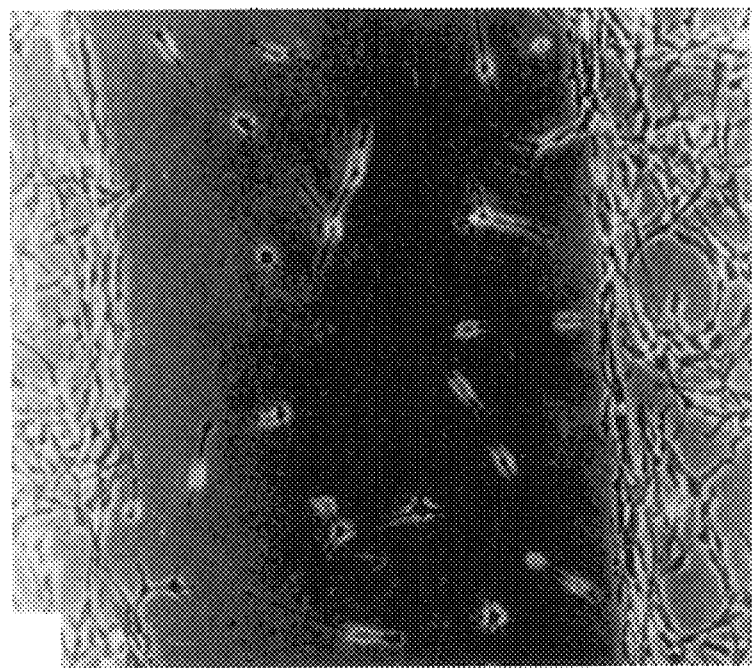
Figure 5C:
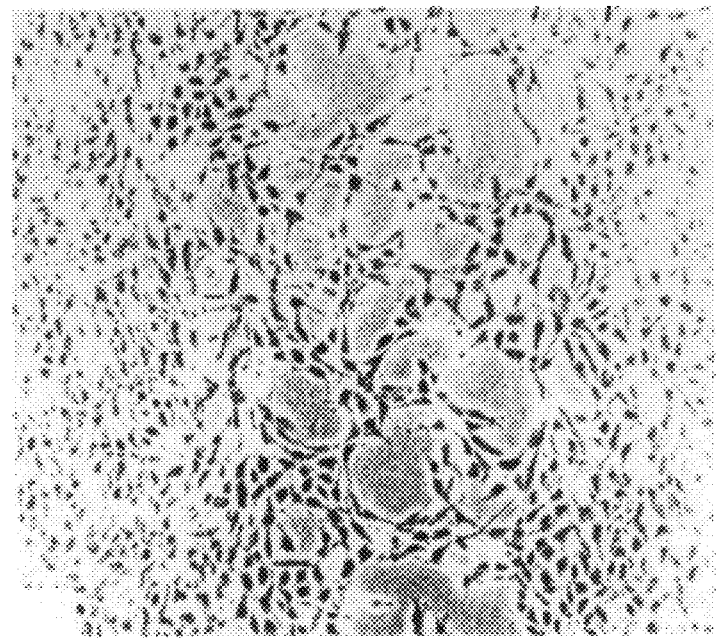
Figure 5D:
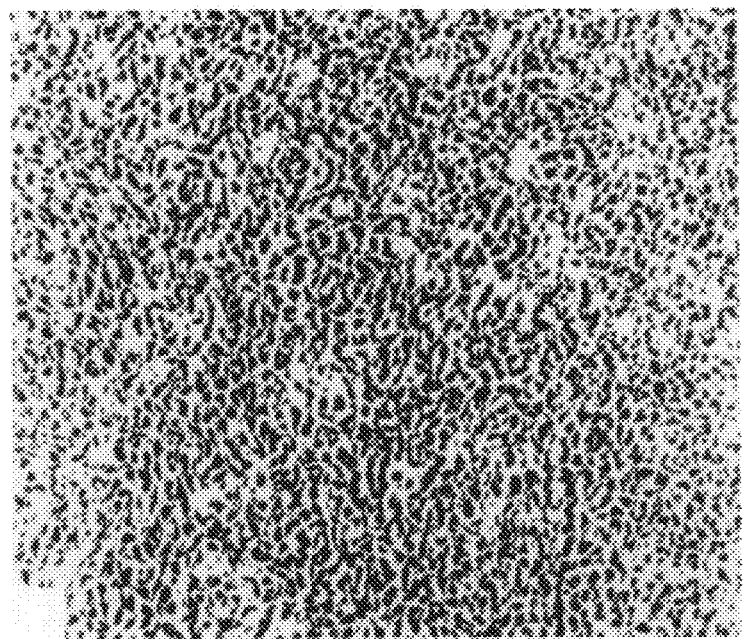

FIGS. 4A–4B. Effect of DS-PG on adhesion and cell migration of DRG explants. Photomicrographs show live DRG explants grown in 60 mm tissue culture dishes coated as described in Section 7.1.2., infra, with alternating bands of LN and DS-PG/LN. (A) 0.8 mg/ml DS-PG, and (B) 0.4 mg/ml DS-PG. The explants in (A) are attached to the stripe containing LN only; no explant adhered to the stripe containing DS-PG. Note the dramatic inhibition of cell migration, most likely by solubilized DS-PG. In the presence of 0.4 mg/ml DS-PG, the explants adhere to the LN stripe and cell migration occurs on it but no cell adhesion, migration or invasion is seen on the DS-PG/LN band. (100×)

FIGS. 5A–5D. Time dependent effect of KS/CS-PG on C6 cell adhesion, migration and invasion. Photomicrographs of live C6 cells grown in 60 mm tissue culture dishes coated as described in Section 7.1.2, infra, with alternating bands of LN and KS/CS-PG/LN at 2.7 mg/ml for (A) 2 hrs, (B) 1 day, (C) 2 days, and (D) 3 days. Note the lack of adhesion to the KS/CS-PG coated band for the first 2 hrs following plating and the stability of the formed band for 24 hrs following plating. C6 invasion of the KS/CS-PG band occurs 2 days after plating and no evidence of preferential adhesion is evident on day 3. (100×)

FIGS. 6A–6D. Effect of heparin, dextran sulfate and dextran on cell migration from DRG explants. Photomicrographs of live DRG explant cultures after 24 hrs of growth in culture medium containing 10% FCS in DMEM/F12, supplemented with 50 ng/ml NGF. Test solutions were added to the culture medium at the time of plating and the effect on neuronal and non-neuronal cell migration is shown. (A) vehicle control, (B) 400 $\mu$g/ml heparin, (C) 200 $\mu$g/ml dextran sulfate, (D) 400 $\mu$g/ml dextran. Note the inhibition of cell migration by heparin and thedramatic inhibition by dextran sulfate. (100×)

FIG. 7. Effect of sulfated carbohydrates on fibroblast and 3T3 cell adhesion. Primary cultures of rat meningeal fibroblasts (RMF) and 3T3 cells were plated on PLL coated 96-well microtiter plates, incubated for 4 hrs in the present of the test compounds and processed for the colorimetric cell adhesion assay as described in Section 7.1.5, infra. The data represent the results obtained from an average of 6 replicates per sample (S.E. did not exceed ±5%). The experiment was repeated twice with essentially the same results.

Figure 8:
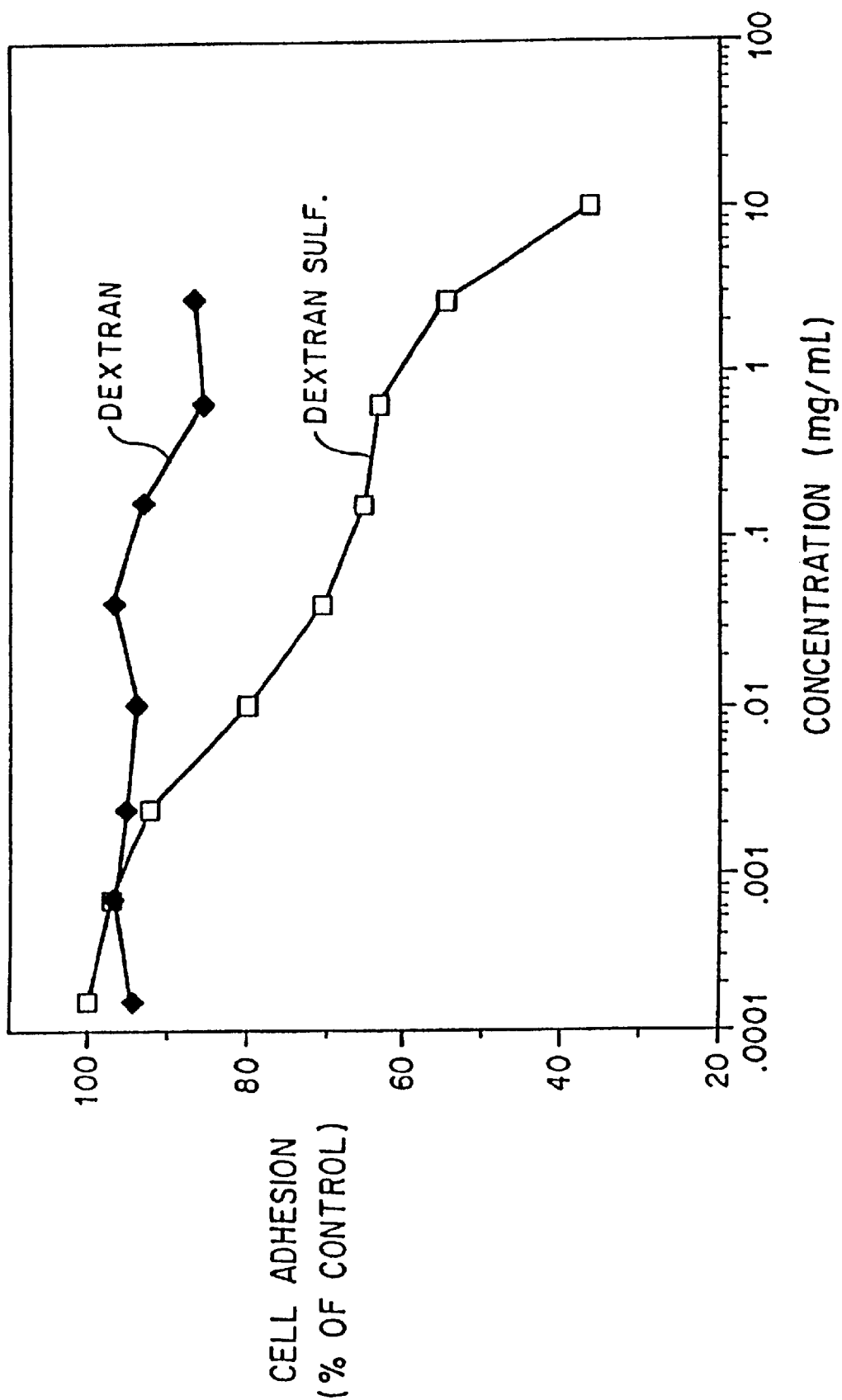

FIG. 8. Dose-response curve of dextran sulfate effect on 3T3 cell adhesion. 3T3 cells were plated on PLL coated 96-well microtiter plates, incubated for 24 hrs in the presence of various concentrations of dextran sulfate or dextran and processed for the colorimetric cell adhesion assay as described in Section 7.1.5., infra. Each point represents the average of three replicates.

Figure 9:
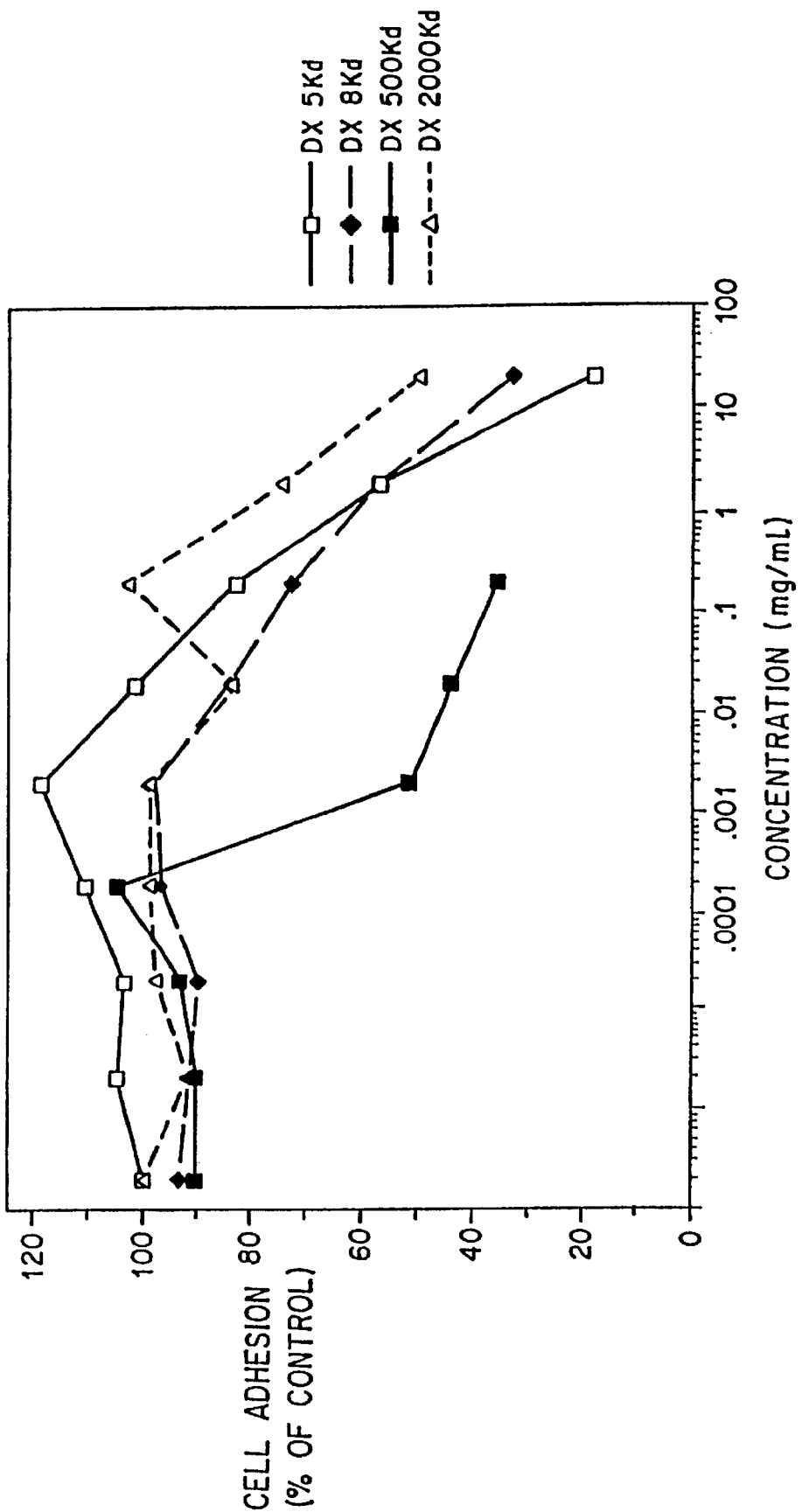

FIG. 9. Dose-response curves for dextran sulfate of different molecular weights: effect on 3T3 cell adhesion. 3T3 cells were plated on poly-L-lysine coated 96-well microtiter plates, incubated for 24 hrs in the presence of various concentrations of dextran sulfate and processed for the colorimetric cell adhesion assay as described in section 7.1.5, infra. Each point represents the average of three replicates.

5. DETAILED DESCRIPTION OF THE INVENTION

The present invention relates to the discovery that certain biocompatible anionic polymers can effectively inhibit scar formation, in particular surgical adhesions, and that these anionic polymers, termed "inhibitory anionic polymers," generally inhibit fibrosis. The invention is predicated on the discovery that anionicpolymers effectively inhibit invasion of cells associated with detrimental healing processes, i.e., fibrosis, and scarring. In particular, anionic polymers of the present invention are useful to inhibit fibroblast invasion, thus regulating the healing process and preventing fibrosis. The anionic polymers of the present invention can also inhibit glial cell invasion, bone growth, neurite outgrowth and monocyte/macrophage invasion. The present invention further relates to the discovery that the effectiveness of an anionic polymer at inhibiting cell, e.g., fibroblast, invasion correlates in part with the effective number of anionic charge groups on the polymer. Thus the present invention teaches a large number of materials for use in inhibition of scar formation and fibrosis, and surgical adhesions. Other anionic polymers for use in the invention may be identified based on effective anionic charge content or density.

Inhibitory anionic polymers for use in the invention include dextran sulfate (DX) and pentosan polysulfate (PS). Additionally, natural proteoglycans, or the glycosaminoglycan moieties of proteoglycans, including dermatan sulfate (DS), chondroitin. sulfate (CS), keratan sulfate (KS), heparan sulfate (HS) and heparin (HN) may be used. The anionic carbohydrate alginate (AL) may also be used. At suitable concentrations, the foregoing molecules can inhibit fibroblast invasion or migration, even in the presence of suitable migration promoting substrates, such as laminin. Other anionic polymers for use in the present invention include cellulose derivatives. In a preferred embodiment, the present invention is directed to methods of using DX, and molecules and compositions comprising DX, to inhibit, prevent or regulate fibroblast invasion and fibrosis and therapeutically, where the foregoing is desired. The invention is further directed to methods of using one or more of the anionic polymers, and compositions comprising one or more of the anionic polymers, to inhibit fibroblast invasion and fibrosis and therapeutic uses thereof. Such molecules comprising KS, CS, DS, HS, or HN include but are not limited to the disaccharide, glycosaminoglycan, and proteoglycan structures.

The instant invention further provides pharmaceutical compositions comprising inhibitory anionic polymers or inhibitory anionic polymers and an adhesive protein, and a pharmaceutically acceptable carrier, and methods to administer the compositions to inhibit scar formation, and fibrosis in general, and to inhibit undesired invasion of glial cells, bone growth, and neurite outgrowth.

The compositions and methods of the present invention are suitable for treatment of animals, preferably mammals, and more preferably humans. A therapeutically effective amount of a composition comprising an anionic polymer of the invention can be administered to a lesion in an animal for any of the methods disclosed infra.

5.1. Other Anionic Polymers for use in the Invention

In addition to dextran sulfate, pentosan polysulfate, the glycosaminoglycans and other anionic polymers for use in the invention (supra), the instant invention provides additional anionic polymers for use in the invention based on the discovery that, in part, the effective anionic character of a polymer helps determine its inhibitory potential (see Section 7., infra). In one embodiment, such an anionic polymer suitable for use is an anionic polymer comprising an acidic sulfate, in which sulfur content is greater than about 5% by weight. In a more preferred embodiment, the sulfur content is greater than about 10% by weight.

Anionic polymers for use in the present invention may be found abundantly in nature, e.g., the proteoglycans. Alternatively, polymers may be chemically derivatized to create an anionic polymer. For example, the polyglucose polymer dextran may be treated by boiling in sulfuric acid and esterifying with chlorosulfonic acid to produce dextran sulfate (see, e.g., The Merck Index, 10th Edition, 1983, No. 2915, page 427). Other examples of anionic polymers prepared chemically include the cellulose derivatives. Polymer backbones are not limited to carbohydrate polymers. Biocompatible anionic polymers may be obtained from commercial sources (e.g., see Section 7.1.6., infra). Alternatively, anionic polymers for use in the present invention may be purified from natural sources or prepared synthetically.

5.2. Compositions to Prevent Fibrosis and Cell Invasion

The invention provides compositions for use in inhibiting fibroblast invasion, glial cell invasion, neurite outgrowth, bone growth, and monocyte/macrophage invasion. In particular the compositions are useful in preventing fibrosis and scar formation, e.g., surgical adhesions. The compositions comprise inhibitory anionic polymers of the invention. Where the composition is intended for use in a therapeutic method or treatment, it may be prepared as a pharmaceutical composition comprising a therapeutically effective amount of an anionic polymer and a pharmaceutically acceptable excipient or carrier, i.e., suitable for use in vivo. The anionic polymer should preferably be present at a concentration greater than about 1 mg/ml. The compositions of the invention are hereinafter referred to as "inhibitory compositions," since they comprise an anionic polymer inhibitor of cell invasion.

For example, in an inhibitory composition of the invention, the anionic polymer may comprise dextran sulfate (DX), keratan sulfate (KS), dermatan sulfate (DS), chondroitin sulfate (CS), heparin (HN), heparan sulfate (HS), alginate (AL), or pentosan polysulfate (PS). In a preferred embodiment, the anionic polymer is dextran sulfate or pentosan polysulfate. In a more preferred embodiment, the anionic polymer is dextran sulfate, in which the sulfur content is greater than about 10% by weight. In an even more preferred embodiment, the average molecular weight of the dextran sulfate is about 40,000 to 500,000 Daltons. The dextran sulfate should preferably be present at a concentration of 2–20 mg/ml.

Carriers or excipients for use with the foregoing anionic polymers include aqueous solutions, such as water, saline, physiologically buffered saline, dextrose solution, or any such carrier known in the art. The admixture of anionic polymer with the carrier may yield a viscous liquid or gel. To increase the viscosity of the liquid or gel, the anionic polymer may be cross-linked using any cross-linking agent known to one of skill in the art, provided that the cross-linked anionic polymer substantially retains its anionic character, i.e., that the negative charge density of the polymer is not substantially affected.

In another embodiment, the biocompatible anionic polymer of the invention may be combined with a solid or semi-solid excipient or carrier, such as paste, gel, foam or sheet. The anionic polymer of the invention may be mixed with said carrier or excipient in a colloidal suspension or admixture; alternatively, the carrier or excipient may be impregnated with the anionic polymer to form the composition.

The invention provides for use of any of the following anionic polymers, including DX, DS, KS, CS, HN, HS, hyaluronic acid (HA), PS, or AL, or any anionic polymer found to be suitable, e.g., see Section 5.1 supra, in combination with the foregoing carriers.

In a preferred embodiment, the anionic polymer may be dextran sulfate or pentosan polysulfate. In a preferred embodiment, the carrier or excipient may be a pharmaceutically acceptable carrier or excipient, i.e., suitable for use in vivo. Preferred semi-solid carriers include dextran gels, such as HYSKON-70 (Pharmacia), INTERCEED® (Johnson & Johnson), native collagen gels, and denatured collagen gels, such as GELFOAM® (Upjohn).

In one embodiment, the GELFOAM® may be soaked with a solution of 2–20 mg/ml dextran sulfate in calcium/magnesium-free phosphate buffered saline (see section 6., infra).

5.2.1. Compositions of Inhibitory Molecules with Adhesive Proteins: Inhibitory-Adhesives In a particular embodiment, the inhibitory anionic polymer may be used in combination with a suitable concentration or amount of an adhesive protein or proteins, the combination producing an "inhibitory-adhesive", to effect the therapeutic functions disclosed infra in Section 5.3. Use of the inhibitory molecule associated with an adhesive protein would preclude dispersion of the inhibitory molecule since the adhesive protein would serve to anchor the inhibitory molecule in place. A suitable concentration or amount of an adhesive protein is a concentration or amount necessary to demonstrate adhesive properties.

As used herein, the term "adhesive protein" refers to a protein or peptide capable of non-specifically adhering to one or more molecules or surfaces. Any natural, unnatural or recombinant protein, containing a substantial amount of dihydroxyphenylalanine (DOPA) and hydroxyl-containing amino acid residues, such that the protein may be activated and cured (see infra), may be used in the invention. Applicants envision that functional peptides as well as whole proteins may be used in the invention. A functional peptide is one that contains a minimum number of amino acids that produce the adhesive properties of the protein. For example, and not by way of limitation, the adhesive protein may be fibrin or commercially available fibrin based products such as TUSSUCOL®, TISSEEL® or HUMAN IMMUNO®. Alternatively, the adhesive protein may be mussel polyphenolic adhesion protein, barnacle polyphenolic adhesion protein, or oyster polyphenolic adhesion protein. Certain bioadhesive proteins are commercially available, e.g., ADHERACELL® (Genex Corp., Gaithesburg, Md.) and MAP ("mussel adhesive protein," Bio-Polymers, Inc., Farmington, Conn.). The adhesive protein may comprise the DOPA-protein from *Phragmatopoma californica* or *Fasciola hepatica* (liver fluke). Polyphenolic adhesion protein from mussel, barnacle or oyster may be extracted and purified from the phenolic gland of the animal, or it may be recombinantly produced (International Patent Publications WO 88/03953, 1988, and WO 88/07076, 1988; Strausberg et al., 1989, in "Adhesives from Renewable Resources", ACS Symposium Series 385, Hemingway and Conner, Eds., pp. 453–464).

It is contemplated that fragments of polyphenolic adhesion protein from mussel, barnacle, or oyster, produced by chemical or proteolytic cleavage of the extracted natural molecule or recombinantly, may be used in the pharmaceutical compositions of this invention. In another embodiment, the adhesive protein may be chemically polymerized peptides from an adhesion protein, e.g, proteolytic or chemical digestion followed by glutaraldehyde polymerization of fragments of the Mytilus edulis protein (U.S. Pat. No. 4,585,585).

In yet another embodiment, the adhesive protein may be an analog of the adhesion protein produced recombinantly. The recombinantly produced analog adhesion protein may be derived from mussel, barnacle or oyster polyphenolic adhesion protein, or any other adhesive protein. Fragments and analogs of adhesion proteins incorporating conservative amino acid substitutions may be used as adhesive proteins in the practice of this invention. The recombinantly produced analog adhesion protein may comprise portions of more than one adhesion protein from mussel, barnacle or oyster, or *Phragmatonoma californica, Fasciola hepatica*, or any other comparable adhesion protein. If necessary, an adhesive protein may be hydroxylated chemically or enzymatically. For example, treatment of tyrosine with mushroom tyrosinase or *strentomyces antibioticus* can modify an adhesive precurser protein. Thus, the pharmaceutical compositions of this invention may comprise a purely engineered adhesion protein that incorporates the principles of naturally occurring adhesion proteins.

In one embodiment, the inhibitory molecule and the adhesive protein may be non-covalently associated prior to activation and curing of the adhesive protein. In another embodiment, the inhibitory molecule may be covalently bound to the adhesive protein prior to activation and curing.

The adhesive proteins of the invention must be cured to allow adhesion to the desired surface curing comprises activating an inhibitory-adhesive composition, specifically the adhesive protein, followed by allowing reaction of the activated adhesive protein with the desired molecule. Enzymatic or chemical processes initiate curing. In the case of polyphenolic adhesion proteins, curing may be initiated by oxidation of DOPA to quinone. Oxidation may result from air exposure, treatment with an enzyme, e.g., catechol oxidase, or by a commercial oxidase cross-linking agent, e.g., COX (Bio-Polymers, Inc.). The foregoing are provided as examples and not by way of limitation; one of skill in this art will know of other oxidative agents or processes. Fibrin curing is initiated by cleavage of fibrinogen, e.g, by thrombin. Fibrin monomers spontaneously polymerize; further action by a transaminase catalyzes covalent cross-linking. The curing process is completed as the activated protein bonds covalently or non-covalently to molecules or surfaces of the surrounding environment.

Thus, the inhibitory-adhesive composition may be applied to the lesion site and allowed to cure. Anchoring of the inhibitory molecule at the site by the adhesive protein would increase the efficacy of the inhibitory molecules by extending the period of local efficacious concentration, thereby more effectively inhibiting incidence of fibroblast invasion and fibrosis, glial cell invasion, neurite outgrowth and bone growth. Beneficial results would be expected when compositions of inhibitory molecule and adhesive protein are applied and cured at the site of surgical incisions, wounds, and general trauma.

5.3. Therapeutic Methods

The compositions provided by the instant invention may be used to treat a variety of conditions where a method for treatment of an animal in which inhibition of fibroblast invasion and fibrosis, granulation, and in particular scar formation, is desired. Methods to inhibit fibrosis, granulation or scar formation of a lesion comprising administering an inhibitory composition or inhibitory-adhesive composition to the site of the lesion are provided. Methods to administer the pharmaceutical compositions for therapeutic treatment are also provided.

5.3.1. General Indications

The inhibitory compositions comprising an inhibitory anionic polymer or inhibitory-adhesive composition can be used as barriers to cell migration or invasion caused by trauma, surgery, infection (viral or bacterial), metabolic disease, malignancy, exposure to toxic agents, and other hyperplastic situations. The inhibitory compositions provide a preferred method to protect an organ or tissue from the previously mentioned conditions through a coating procedure. For example, dorsal root ganglia, optic nerve, or optic chiasma may be coated with the inhibitory composition in order to protect against uncontrolled cell invasion and adhesion. Glial cell invasion, neurite outgrowth, and bone growth, as well as fibroblast invasion, can be inhibited by the methods of the present invention. Coating an organ or tissue with an inhibitory composition may be preventive or prophylactic. Inhibitory-adhesive compositions provide a preferred coating composition.

5.3.2. Surgery

In one embodiment, epidural (or peridural) fibrosis may be inhibited by application of a composition of the instant invention to the surgical lesion. In one embodiment, a section of collagen gel soaked with a solution containing an anionic polymer of the invention may be applied to the lesion. In another embodiment, the anionic polymer may be applied in a carrier or excipient such as a paste, gel, or sheet. In yet another embodiment, the anionic polymer may be dissolved or suspended in a carrier such as physiologically buffered saline, and applied by irrigation or as an aerosol. In a preferred embodiment, a pharmaceutical carrier or excipient may be used.

The present invention provides materials and methods for inhibiting fibrosis following laminectomy, in particular inhibiting epidural (peridural) fibrosis following a lumbar laminectomy (see Section 6., infra). By way of illustration, not limitation, segments of semi-solid pharmaceutically acceptable carrier are soaked with dextran sulfate, or another anionic polymer of the present invention. The soaked carrier may be prepared beforehand or at the time of surgery. The carrier may be soaked in a solution of dextran sulfate, or another anionic polymer for use in the invention, in calcium/magnesium-free phosphate buffered saline (CMF-PBS), or any solution suitable for in vivo use. After impregnating the carrier with the anionic polymer, segments are inserted into the laminectomy site. Using the foregoing method, at reoperation, the site of the laminectomy will show minimal scar tissue formation and bone growth, the carrier may be easily removed, and the dura mater may be visible as a smooth transparent membrane. The anatomic features associated with detrimental fibrosis, i.e., scarring and surgical adhesions that tether the nerve roots, will be absent.

The anionic polymers of the invention, and compositions comprising the same, also have use in inhibiting undesirable bone growth by administering a therapeutically effective amount of anionic polymer to a site where inhibition of bone growth is desired (see Section 6., infra). Furthermore, the anionic polymers may be used to treat other indications where inhibition of bone growth is desirable. This is especially true in children, where bone growth following certain procedures, such as craniostemostosis, is undesirable.

In yet another embodiment, the present invention provides a composition and method to inhibit fibrosis and scarring of fallopian tissue. In particular, fibrosis and scarring of lesions in and around the fallopian tube subsequent to surgery can be inhibited. Fibrosis of fallopian tubes, resulting from infection or other causes, is a cause of infertility in 25–30% of the cases. Pelvic sidewall adhesions are also implicated in infertility. Since scar tissue forms subsequent to surgery, surgical removal of adhesions alone is not adequate treatment. Thus the present invention has an important application in management of infertility.

The following example suggests one of many uses of the invention in treatment of fallopian tissue after surgery. Compositions comprising an anionic polymer can be tested for their ability to inhibit fibrosis of uterine horn of the rat after standarized traumatic lesions. The abdominal skin and muscle of an animal model, e.g., a female Lewis rat, may be incised to open the peritoneal cavity. An incision may be made in the wall of the uterine horn. The endometrium is subjected to a standardized traumatric lesion and then a semi-solid pharmaceutically acceptable carrier soaked with a suitable anionic polymer, e.g., dextran sulfate, may be inserted at the site of the lesion.

In a preferred method to treat fallopian tissue after surgery, a gel or paste comprising an anionic polymer may be inserted, such that the inhibitory composition will naturally be resorbed by the body subsequent to healing of the lesion or be flushed out by hydrotubation. After insertion of the inhibitory composition, the abdominal muscles and fascia are closed and sutured. The skin incision is also closed.

One of ordinary skill would recognize from the foregoing that the present invention provides a preferred method of treatment in conjunction with any surgery. The foregoing methods may be used to inhibit fibrosis, scar formation and keloid formation after surgery. The methods of the invention will be useful for surgical procedures where minimal scarring is desired, especially for plastic, i.e., reconstructive or cosmetic surgery. Other surgical indications include but are not limited to abdominal surgery, joint surgery, tendon surgery, surgery to remove pelvic sidewall adhesions, peritoneal surgery, thoracic surgery, vascular surgery, and cardiac surgery, in particular bypass surgery, valve replacement surgery, cardiovascular surgery, or other open heart surgery.

The present invention further provides a treatment of hypertonic and keloid scars. Disfiguring and mobility-limiting scars often return after surgical removal. Application of inhibitory or inhibitory-adhesive compositions can limit or prevent hypertonic scar or keloid formation after treatment to remove a scar.

In yet another embodiment, the anionic polymers of the invention may be used in a method of inhibiting fibrosis around an implant comprising applying a composition comprising a therapeutically effective amount of an anionic polymer of the invention to the implant. Examples of implants where inhibition of scar formation and fibrosis is desired include, but are not limited to, nephrostomy tube, peritoneal drainage tube, artificial hip joint, artificial heart valve, peripheral nerve repair and other prostheses and intravenous catheter. Implants may be treated by coating or impregnating with a composition provided by the invention. The invention further provides an improved implant, in which the improvement comprises a coating on the implant, which coating consists of a suitable amount of an inhibitory-adhesive composition. Implants may be polymer implants. Said polymer implants can have various compositions, pore sizes and geometries, and may include, but are not limited to, biocompatible polymers made of nitrocellulose, polyanhidrides, and acrylic polymers. The polymer forming the implant may itself be an anionic polymer.

5.3.3. Treatment of Fibrotic Lesions in Joints

The inhibitory compositions of the present invention may be used in the treatment of various fibrotic joint lesions. Traumatic injuries often result from physical exertion and contact associated with athletics. Fibrosis of joints resulting from traumatic injury, such as a fall or collision, renders the injured joint stiff and movement painful. Scar tissue forms in the traumatized area after tendon damage. In temporomandibular joint dysfunction, jaw movement is limited and may be painful.

One method to treat joint lesions is to open the joint surgically or access the joint arthroscopically and remove the adhesions. These processes have the disadvantage of inducing further fibrosis during the healing process.

Administration of a composition comprising an inhibitory anionic polymer of the present invention would inhibit subsequent fibrosis and adhesion formation in the joint, thus increasing the chance of successful therapy.

The invention will be of use to orthopedic surgeons in the treatment of joint damage resulting from athletics or accidents. Oral surgeons will find the invention useful in the treatment of some forms of temporomandibular joint dysfunction. Anionic polymers for use in methods of treatment are described in Section 5. and 5.1., supra, and compositions are described in Section 5.2. and 5.2.1., supra. In a preferred embodiment, dextran sulfate, in which the sulfur content is greater than 10% by weight, may be used. In a more preferred embodiment, the average molecular weight of the dextran sulfate is about 40,000 to 500,000 Daltons.

5.3.4. Inhibition of Glial Cell Invasion

Theanionic polymers of the present invention, such as dextran sulfate, pentosan polysulfate, alginate, and anionic polymers with a high degree of anionic character, e.g., sulfated anionic polymers of greater than about 10% sulfur content wherein the sulfur is found as acidic sulfate, are useful in a method of inhibiting glial cell invasion comprising administering said anionic polymer to the site where inhibition of glial cell invasion is desired. In various embodiments, the glial cell invasion is caused by a disease or disorder such as trauma, surgery, viral infection, bacterial infection, metabolic disease, malignancy, exposure to toxic agents, or hyperplastic situations. The glial cell may be an astrocyte.

In another embodiment, the inhibitory-adhesive compositions can be used as barriers to glial cell migration or invasion. The inhibitory-adhesive compositions provide a preferred method to protect an organ or tissue from the previously mentioned conditions through a coating procedure. For example, dorsal root ganglia, optic nerve, or optic chiasma may be coated with the inhibitory-adhesive composition in order to protect against uncontrolled cell invasion and adhesion. Fibroblast as well as glial cell invasion would be inhibited by this method. Coating an organ or tissue with inhibitory-adhesive may be preventive or prophylactic, or may be a treatment in patients where a disorder has already been manifested.

5.3.5. Inhibition of Neural Cell Invasion

Methods of inhibiting cell invasion by administering anionicpolymers with a high degree of anionic character, e.g., sulfated anionic polymers of greater than about 10% sulfur content and pharmaceutical compositions comprising the same, can be used for inhibition of neurite outgrowth. In a particular embodiment, an inhibitory-adhesive composition may be used. The anionic polymer may be administered to the area where inhibition of neurite outgrowth or glial cell invasion is desired. In one embodiment, the inhibitory composition may be used in the treatment of patients with gliomas, or tumors of nerve tissue, e.g., malignant tumors such as neuroblastoma.

In another embodiment, an inhibitory composition can be used for the treatment of a neuroma (undirected axon growth associated with situations where the axon is missing either its appropriate target or substrate pathway for neural development). For example, the inhibitory composition may be used for treatment of neuroma associated with amputation, lesion or congenital deformities, to mention but a few conditions. Currently, a hole is drilled in nearby bone and the axon placed in the hole. Frequently, this method fails because the axon disengages from the hole, and a neuroma forms. Use of an inhibitory composition of the invention to coat the nerve ending and the bone would overcome this current deficiency by providing an environment inhibitory to undirected axon growth. Alternatively, the inhibitory composition may be used in a polymer "cap", i.e., a polymer cylinder with one closed end. An anionic polymer of the present invention may be used to coat the interior of the cap, thus providing an environment inhibitory to neurite outgrowth and neuroma formation. In another embodiment, the polymer cap may comprise an anionic polymer.

In a preferred embodiment, an inhibitory-adhesive composition may be used for treatment of neuroma. Use of the inhibitory-adhesive composition of the invention to coat the axon and the bone would (1) anchor the axon into the hole in the bone, and (2) provide an inhibitory environment. Alternatively, the inhibitory-adhesive composition may be used to anchor the nerve ending in a polymer "cap".

Disorders resulting from an overproduction of nerve growth-promoting factors, including but not limited to nerve growth factor, ciliary neurotrophic factor, brain-derived growth factor, laminia, NCAM, L2, and SSEA-1 can also be treated by administration of an inhibitory or inhibitory-adhesive composition. The inhibitory or inhibitory-adhesive compositions can be used to treat disorders of the central and/or peripheral nervous systems.

5.3.6. Modes of Administration

Methods of introduction of the inhibitory anionic polymers or the inhibitory-adhesive compositions of the invention include methods known to those skilled in the art. It may be desirable to introduce the inhibitory compositions or inhibitory-adhesive compositions of the invention into the site of interest by any suitable route. This may be achieved by, for example, but not by way of limitation, local infusion or application during surgery, by injection, by aerosol, by means of a catheter, or by means of an implant, said implant being of porous, non-porous, or gelatinous material, including membranes, such as silastic membranes, or fibers. In a preferred embodiment, the implant is coated or impregnated with an inhibitory-adhesive composition of this invention. Polymer implants treated with inhibitory molecule or, more preferably, coated with inhibitory-adhesive, can be applied or inserted at the desired site of treatment. Such polymers can have various compositions, pore sizes, and geometries. Polymers that can be used include but are not limited to those made of nitrocellulose, polyanhydrides, and acrylic polymers.

The invention provides for application of an inhibitory composition or inhibitory-adhesive composition by surgical procedures. The inhibitory anionic polymer or inhibitory-adhesive may be applied to a surgical wound. The anionic polymer or inhibitory-adhesive may be directly applied to sites of tissue injury, or to coat an entire organ or to close a surgical incision. Where suitable, administration of the inhibitory anionic polymer or inhibitory-adhesive composition may be made by orthroscopic procedures.

It is envisioned that where the inhibitory-adhesive compositions are introduced, the adhesive protein will have the opportunity to cure (see Section 5.2.1, supra) at the desired site and anchor the inhibitory molecule for optimum effectiveness. Curing may occur in an air environment, such as when the inhibitory-adhesive composition is applied to a surgical incision, traumatic wound, or to an organ or tissue during classical open surgery. Alternatively, curing may occur in situ by exposure to weak oxidative molecules or naturally, where viscosity of the composition is such that the composition remains in proximity of the desired site while curing takes place.

6. EXAMPLE

Epidural Fibrosis Animal Model

Epidural fibrosis refers to the scar tissue that forms following a laminectomy procedure. Scar tissue forms within the laminectomy site and binds the undersurface of the erector spinae muscles to the posterior and lateral surfaces of the dura mater and to the nerve roots exiting through the dura matter. The scar tissue attachment to the nerve roots is believed to be the cause of long-term, recurrent pain following laminectomy procedures.

Epidural fibrosis was investigated after lumbar laminectomy in rats. In this model, a laminectomy was performed at the lumbar 3 and 5 vertebrae and then the test agent was applied to the laminectomy site. Subsequently, the laminectomy sites were examined for fibrosis by gross dissection or by histological analysis.

6.1. Materials and Methods 6.1.1. Experimental Design

Laminectomies (described below) were performed at lumbar vertebrae L3 and L5 to provide auto-controls within each animal. Segments of GELFOAM® (Upjohn) soaked with experimental or control solutions were inserted into the laminectomy site. The soaked GELFOAM® fragments were prepared and coded 24 hours beforehand. The GELFOAM® segments were soaked in solutions of dextran sulfate in calcium/magnesium-free phosphate buffered saline (CMF-PBS), dextran in CMF-PBS, or CMF-PBS alone. In some laminectomy sites, the GELFOAM® fragments were omitted, in order to serve as sham operations. Subsequently, the evaluation by gross dissection was done without knowledge of which solutions had been placed in which laminectomy site. Thus, the experiments were double-blind.

6.1.2. Laminectomy

Lewis inbred rats were anesthetized with 4% chloral hydrate (34 mg/100 g body weight). The dorsal skin was incised and the paraspinal muscles were separated from the spinous processes of lumbar vertebrae L2 through L6. The spinous processes of L3 and L5 were removed with a rongeurs; then the vertebral lamina was removed with a micro-rongeurs creating a rectangular laminectomy defect 4×2 mm in size. After bleeding was stopped, a GELFOAM® segment was placed into the laminectomy site according to a randomized protocol. The overlying paraspinal muscles were closed over the site by suturing the superficial fascia together with resorbable 6-0 PDS II (Ethicon). The skin incision was closed with wound clips.

6.1.3. Analysis

The animals were kept for two weeks prior to gross evaluation. At that time, the rats were anesthetized with 4% chloral hydrate and the wound was reopened by incising the skin and separating the paraspinal muscles. The quality and quantity of scar tissue above the laminectomy site, the appearance of the GELFOAM® and the extent of new bone growth was evaluated by visual and tactile observation during sharp dissection. After the gross evaluation was complete, the rats were euthanized by anesthesia overdose.

6.2. Results

All gross evaluations were made prior to breaking the treatment code, but the observations have been tabulated and presented below according to treatment group. The criteria for evaluating and quantitating the extent of epidural fibrosis are shown in Table 1.

TABLE 1

CRITERIA FOR GROSS EVALUATION

| | |
|---|---|
| Superficial Scar | 1 - Thin and friable |
| | 2 - Medium thickness |
| | 3 - Thick and tough |
| Appearance of | 0 - Removed in one piece |
| Gelfoam ® | 1 - Removed in several clumps |
| | 2 - Partially attached to surrounding tissue |
| | 3 - Firmly attached and difficult to remove |
| Deep Scar | 0 - Dura mater clearly visible |
| | 1 - Thin layer of scar tissue over dura mater |
| | 2 - Medium layer of scar tissue over dura mater |
| | 3 - Thick layer of scar tissue over dura mater |
| Bone Growth | 0 - No new bone growth over laminectomy site |
| | 1 - Minimal bone growth over laminectomy site |
| | 2 - Medium bone growth over laminectomy site |
| | 3 - Thick bone growth over laminectomy site |

In all animals, the skin incision and the underlying fascia and paraspinal muscles had healed well. At all laminectomy sites, separation of the paraspinal muscles revealed a layer of scar tissue.

At dextran sulfate sites, the superficial scar tissue was found to be a thin layer and it was easily peeled away from the underlying GELFOAM®. The GELFOAM® could be readily removed from the laminectomy site in one or two pieces. After removal of the GELFOAM®, the dura mater was visible as a smooth and transparent membrane. The laminectomy site itself had not changed appreciably in size; the borders of the site appeared smooth.

The negative control sites (dextran or CMF-PBS) were dramatically different. The first difference was noted in the superficial layer of scar tissue: this layer adhered to the GELFOAM®. As the scar tissue was removed, bleeding began in and around the GELFOAM® (bleeding did not occur when removing dextran sulfate-soaked GELFOAM®). Another difference was the texture of the GELFOAM®: it was very friable and fell apart as we removed it. After removal of the GELFOAM®, it was obvious that the size of the laminectomy site had dramatically decreased to a narrow slit. The texture and hardness of the laminectomy border indicated that the laminectomy site had narrowed because of new bone growth.

TABLE 2

EPIDURAL FIBROSIS: GROSS ANATOMICAL EVALUATION

| Agent | Superficial Scar | Gelfoam ® Appearance | Deep Scar | Bone Growth | Total Score |
|---|---|---|---|---|---|
| Dextran Sulfate (n = 11) | 1.2 ± 0.4* | 0.1 ± 0.3* | 0.3 ± 0.5* | 0.1 ± 0.3* | 1.7 ± 0.9* |
| Dextran (n = 12) | 2.7 ± 0.5 | 2.2 ± 0.8 | 2.3 ± 0.9 | 1.6 ± 0.9 | 8.8 ± 2.4 |
| Buffer (n = 17) | 2.6 ± 0.5 | 2.4 ± 0.5 | 2.4 ± 0.7 | 1.9 ± 0.8 | 9.3 ± 1.9 |

*Dextran sulfate scores significantly different ($p < 0.001$) from scores of dextran or buffer in the same category.

The results shown in Table 2 compare the effect of dextran sulfate, dextran and phosphate buffer on each individual criterion as well as the total score (a lower score indicates greater inhibition of scar formation). In all four criteria, implantation of dextran sulfate into the laminectomy site resulted in scores that were significantly lower than implantation of either dextran or phosphate buffer. These results demonstrate that dextran sulfate was a dramatically potent agent for reducing epidural fibrosis in the rat laminectomy model.

The effect of different dextran sulfate concentrations upon epidural fibrosis was tested in the rat laminectomy model and scored as described above in Table 1 (Table 3).

TABLE 3

DOSE RESPONSE OF DEXTRAN SULFATE

| CONCENTRATION | TOTAL SCORE |
|---|---|
| 20 mg/ml | 1.3 ± 0.5 |
| 2 mg/ml | 3.0 ± 2.3 |
| 0.2 mg/ml | 7.8 ± 1.9 |
| Control (0 mg/ml) | 9.3 ± 1.9 |

The scar formation was most inhibited by dextran sulfate at a concentration of 20 mg/ml. Reducing the concentration by ten-fold to a concentration of 2 mg/ml slightly reduced the inhibition of scar formation, but the inhibition was still noticeably greater than control. At a concentration of 0.2 mg/ml, dextran sulfate showed inhibition that was not significantly different from control.

The effect of dextran sulfate, dextran and phosphate buffer on inhibition of epidural fibrosis was tested as a function of time after implantation and scored as described in Table 1 (Table 4).

TABLE 4

INHIBITION OF EPIDURAL FIBROSIS AT 2 & 4 WEEKS POST-IMPLANTATION

| AGENT | TOTAL SCORE | |
|---|---|---|
| (20 mg/ml) | 2 WEEKS | 4 WEEKS |
| Dextran Sulfate (n = 4) | 1.2 ± 0.5 | 1.8 ± 0.9 |
| Dextran (n = 4) | 9.5 ± 2.4 | 10.0 ± 1.2 |
| Buffer (n = 4) | 9.5 ± 1.9 | 10.5 ± 0.7 |

The inhibition of scar formation by dextran sulfate was just as strong at 4 weeks as it was at 2 weeks post-implantation (no significant difference). Neither dextran nor buffer showed inhibition of scar formation at either time point. The results indicate that scar inhibition by dextran sulfate is long-lived as well as potent.

Using the rat laminectomy model, several different compositions comprising an anionic polymer were tested-for inhibition of epidural fibrosis. Heparin and hyaluronic acid are polysulfated glycosaminoglycans; pentosan is a polysulfated xylan; and alginate is a carboxylated carbohydrate polymer. The effect of each compound on scar formation was scored as described in Table 1 (Table 5).

TABLE 5

EFFECT OF VARIOUS POLYANIONIC COMPOUNDS ON EPIDURAL FIBROSIS

| AGENT (20 mg/ml) | TOTAL SCORE |
| --- | --- |
| Dextran Sulfate (n = 11) | 1.7 ± 0.9 |
| Dextran (n = 11) | 8.8 ± 2.4 |
| Pentosan (n = 2) | 5.0 ± 1.0 |
| Heparin (n = 4) | 7.3 ± 2.5 |
| Alginate (n = 4) | 7.3 ± 1.9 |
| Hyaluronic Acid (n = 4) | 9.3 ± 0.5 |
| Buffer (n = 17) | 9.3 ± 1.9 |

Of all these compounds, only dextran sulfate showed a potent inhibition of scar formation. Pentosan exhibited partial inhibition of scar formation; heparin and alginate exhibited a marginal improvement over buffer (control). Heparin also caused hemorrhage and hematoma formation in the rats at the laminectomy site, which was not seen with similarly applied dextran sulfate. Hyaluronic acid exhibited no ability to inhibit scar formation.

6.3. Conclusions

The rat epidural fibrosis model clearly shows that the presence of dextran sulfate provides a substantial therapeutic benefit by inhibiting fibrosis and scar formation. The dextran sulfate-treated GELFOAM® also inhibited bone growth. In the foregoing example, treatment of a surgical lesion with dextran sulfate-GELFOAM® prevented all but a thin layer of scar tissue, and the dura mater remained smooth and transparent. The dextran sulfate impregnated GELFOAM® was removed readily in one piece, indicating that fibrosis was prevented. In contrast, the negative control sites showed superficial scarring, a thick and tenacious deep scar, and dense bone growth.

Dextran sulfate as used in this example is an anionic polymer with a high effective anionic charge density and a sulfur content of 15.3% by weight. Dextran sulfate may be prepared by boiling dextran with sulfuric acid and esterifying with chlorosulfonic acid. Both dextran and dextran sulfate have a polyglucose carbohydrate backbone. Comparison of the result with dextran sulfate versus dextran impregnated GELFOAM® indicates that the anionic nature of the polymer influences its inhibitory potential and usefulness in the instant invention since dextran sulfate (highly anionic) was much more effective than dextran (not anionic) at inhibiting epidural fibrosis.

However, the results with other anionic polymers shown in Table 5 indicate that charge density alone does not indicate inhibitory potential in vivo. Natural proteoglycans that are strongly inhibitory in vitro (see Section 7., infra) were minimally active (alginate, heparin) or inactive (hyaluronic acid) in vivo. Pentosan was moderately effective at preventing epidural fibrosis, although it was highly effective at inhibiting cell invasion in vitro.

7. EXAMPLE

Inibition of Cell Invasion In Vitro

Anionic polymers have been found to inhibit cell invasion. The stripe assay (described infra) provides a useful in vitro model for cell invasion. Inhibitory activity may be determined by the level of migration of cells from stripes coated with a substrate molecule such as laminin to stripes coated with the substrate molecule and an inhibiting molecule, e.g., an anionic polymer. The ability of anionic polymers, particularly DS and KS/CS, to inhibit cell adhesion was also determined.

7.1. Materials and Methods

7.1.1. Cell Culture

Cell lines. Murine 3T3 fibroblast (NIH), rat C6 glioma (Paganetti et al., 1988, J. Cell Biol. 107:2281) and MCG-28 young immortalized mouse astrocyte (a murine neonatal astrocyte line immortalized with SV-40) were grown in medium composed of Dulbecco's modified Eagle medium (DMEM), 10% fetal calf serum (Gibco Laboratories), and penicillin G/streptomycin (100 units/ml, 100 µg/ml respectively, Gibco Laboratories). For the stripe assay, confluent plates were disaggregated with 0.05% trypsin, 0.53 mM EDTA (Gibco Laboratories) and seeded at 200,000 cells/ml (3 ml/plate). For the cell adhesion assays, confluent cultures were disaggregated with 0.03% EDTA and plated in a 96-well microtiter plate at 20,000–100,000 cells per well. PC12 cells, a pheochromocytoma cell line (Green L. A. & Tischler A. S., 1976, Proc. Natl. Acad. Sci. U.S.A. 73:2424), were grown in medium containing Roswell Park Memorial Institute (RPMI) medium 1640 (Gibco Laboratories), 10% horse serum, 5% fetal calf serum (FCS), and penicillin G/streptomycin (100 units/ml, 100 µg/ml respectively, Gibco Laboratories). The cells were disaggregated with 0.03% EDTA and plated in a 96-well microtiter plate at 3,000 cells per well.

Primary Cell Cultures. Primary cultures of rat meningeal fibroblasts (RMF) were obtained from P-3 rat pups. The tissue was removed from the animals and transferred to Leibovitz's L-15 with L-glutamine medium. The tissue was then cut into small pieces with a scalpel blade, enzymatically dissociated with 0.25% trypsin in $Ca^{2+}/Mg^{2+}$ free Hank's balanced salt solution (CMF-HBSS, Gibco Laboratories) for 20 minutes at 37° C., and mechanically triturated. The cells were rinsed with DMEM plus 10% FCS, concentrated by centrifugation and subsequently diluted in DMEM with 10% FCS for plating at $5.0\times10^6$ cells per 75 cm² flask. Adult rat sciatic nerve fibroblasts (RSF) were obtained by explantation of 1 mm sections of adult rat sciatic nerve.

Rat astrocytes (RAST) cultures were prepared from P-1-3 rat brain cortices. The cortices were stripped of connective tissue and blood vessels, cut into small pieces and dissociated in 0.5% collagenase (Gibco Laboratories) for 20 min at 37° C., followed by further dissociation in 0.25% trypsin for 15 min, and 0.04 mg/ml DNAse (Sigma) and 0.52 mg/ml soy bean trypsin inhibitor for 5 min at 37° C.

The cells were subsequently mechanically dissociated by trituration with a Pastuer pipette and plated at $1.5\times10^7$ cells in a poly-L-lysine (PLL, Sigma) coated 75 cm² flask.

The flask was shaken 4 hrs following plating to remove less adherent non-astrocytic oligodendrocytes and neurons.

Primary Explant Cultures. Dorsal root ganglia (DRGs) were obtained from E8-E9 chick embryos. The dissection was carried out in CMF-HBSS. The spinal cord was exposed and DRGs were removed and cleaned from surrounding connective tissue. DRGs were plated in DMEM/F12, 10% fetal calf serum containing 50 ng/ml nerve growth factor (NGF). The DRGs were seeded on laminin (LN, Gibco Laboratories) or poly-L-lysine (PLL, Sigma) coated dishes.

7.1.2. Stripe Assay

The stripe assay was performed essentially as described by Snow et al. (1990, Exp. Neural. 309:111–130). Tissue culture Petri dishes (Falcon, 60 mm) were precoated with 0.5 ml of a mixture of 5 cm² section nitrocellulose (Schleicher & Schuell, Type BA 85) dissolved in 6 ml methanol, and air dried in a laminar flow hood. Cellulose filter paper (Whatman #1) was cut into 12×0.35 mm strips with a McIlwain tissue chopper (The Mickle Laboratory Engineering Co., LTD). A strip of filter paper was soaked in 20 µl of a solution of DS-PG or KS/CS-PG and LN at given concentration, blotted onto the nitrocellulose-coated dish for 30 sec, and removed. The test solution was allowed to air dry. This process was repeated several times creating clearly defined, equally spaced parallel bands of uniform width on the plates. A thin layer of 0.1 or 1 mg/ml LN was then spread evenly across the bands with a bent glass Pasteur pipet, and covered with culture medium (FIG. 1).

Plates were seeded with cell suspensions of 2.0×10⁵ cells/ml or 4–10 DRG explants. The cultures were assessed for degree of adhesion, migration and/or invasion of the DS-PG or KS/CS-PG bands over a period of up to 7 days using a Leitz Fluovert microscope.

Bands that were completely inhibitory to cell adhesion, migration and/or invasion were evaluated as (−), those allowing limited cell adhesion, migration and/or invasion (+/−), and those permissive to cell adhesion, migration and/or invasion as (+). Cell adhesion was defined as the initial interaction between the cell surface and the substratum which results in cell attachment and spreading. Cell migration was operationally defined as cell movement within the same substratum, and cell invasion was operationally defined as cell movement from one type of substratum to another type of substratum.

7.1.3. Explant Outgrowth Assay

Explants of DRG were plated on LN or PLL coated dishes and the halos of neuronal and non-neuronal (fibroblast and Schwann cell) outgrowth were observed for 1, 2 and 3 days with a Leitz Fluovert microscope. The relative outgrowth, compared to outgrowth of untreated controls, was rated as follows: 1: 0–19% of control; 2: 20–39% of control; 3: 40–59% of control; 4: 60–79% of control; 5: 80–100% of control.

7.1.4. PC12 Neurite Outgrowth Assay

PC12 cells were primed with 20 ng/ml NGF for 8 days, collected with 0.03% EDTA in PBS and plated in precoated 96-well microtiter plates at 3,000 cells/well. The microtiter plates were precoated with poly-L-lysine and blocked with adhesion medium (1% BSA in RPMI) for 20 min prior to addition of cells. The cells were grown in adhesion medium supplemented with 20 ng/ml NGF. The cells were allowed to attach for 2 hr prior to the addition of the test compounds (Akeson and Warren, 1986, Exp. Cell Res. 162:347–362).

7.1.5. Colorimetric Cell Adhesion Assay

Microtiter plates were precoated with poly-L-lysine and blocked with 1% BSA in DMEM for 20 min prior to addition of cells. The cells were plated on the precoated 96-well plates and test compounds were added to the culture medium. Following 4–24 hr incubation at 36° C., 5% $CO_2$, in a humidified incubator, the tetrazolium salt MTT (3-(4, 5-dimethylthazol-2-yl)-2,5-diphenyl tetrazolium bromide) was added. The cultures were incubated for 2 hr to allow mitochondrial succinate dehydrogenase, found in viable cells, to hydrolyze the MTT to its formazan blue reaction product. The media was aspirated and the wells were rinsed to remove all detached cells. The formazan blue reaction product in attached cells was solubilized with 0.08 N HCl in isopropanol, and the plates were read in a microtiter plate reader (Dynatech MR4000) at 570 nm with a 630 nm reference filter. The resulting optical density readings are directly related to the number of viable cells in the well (Mosmann, T., 1983, J. Immunol. Methods 65:55–63). The samples were run in 3–6 replicates per point and the SD was less than 5%.

7.1.6. Reagents

Heparin, H-7005 Sigma, lot:19FO268 Grade II from porcine, sodium salt; dermatan sulfate 90%, (Chondroitin sulfate B) C-4259 Sigma, lot 59FO848, sodium salt, porcine skin; chondroitin sulfate A, C-0914 Sigma, sodium salt, porcine; dextran sulfate, D-6001 Sigma, lot 50HO458, MW 500 kD; dextran, Sigma, D-5251 Sigma, lot 40HO4211, MW 485 kD; pentosan polysulfate, Sigma, P-8275, lot 114F0194.

7.2. Results 7.2.1. Effect of DS-PG on Cell Adhesion, Migration and Invasion

The effect of DS-PG on cell attachment (i.e., adhesion), migration and invasion was tested using primary cultures and fibroblast and glial cell lines. Cell suspensions were plated on tissue culture plates prepared for the stripe assay as described supra. Culture plates were coated with alternating DS-PG/LN (0.1–0.8 mg/ml, and 20 µg/ml, respectively) and LN (20 µg/ml) stripes, and cell adhesion, migration and invasion was evaluated 2 days following plating.

Stripes of substratum containing a mixture of 0.8 mg/ml DS-PG and 20 µg/ml LN were inhibitory to 3T3 cell adhesion. Cells attached preferentially to regions of the LN substratum that were devoid of DS-PG. The alternating bands of cells formed sharp boundaries at the interface between DS-PG/LN and LN containing stripes (FIG. 2A & B; scored as (−)). At 0.2 mg/ml slight invasion was observed (FIG. 2C; scored as (+/−)), and at 0.1 mg/ml, cells were able to invade and migrate on the bands (FIG. 2D; scored as (+)). The inhibitory effect of DS-PG on cell adhesion, migration and invasion was observed with all cell types tested (Table 6). Both primary cells and cell lines formed bands devoid of cells at 0.8 mg/ml, and with the exception of primary astrocytes, at 0.4 mg/ml DS-PG. The effect was dose dependent, demonstrating reduction in inhibition at approximately 0.2 mg/ml and loss of inhibition at 0.1 mg/ml DS-PG.

TABLE 6

Dose and Cell-type Dependent DS-PG Effect on Adhesion, Migration and Invasion

| Dose (mg/ml) | Cell Type | | | | | | |
|---|---|---|---|---|---|---|---|
| | RMF | RSF | 3T3 | RAST | C6 | MCG28 | DRG |
| 0.8 | − | − | − | − | − | − | − |
| 0.4 | − | − | − | +/− | − | − | − |
| 0.2 | +/− | +/− | +/− | +/− | +/− | + | +/− |
| 0.1 | + | +/− | + | + | + | + | + |

Figure 3A:
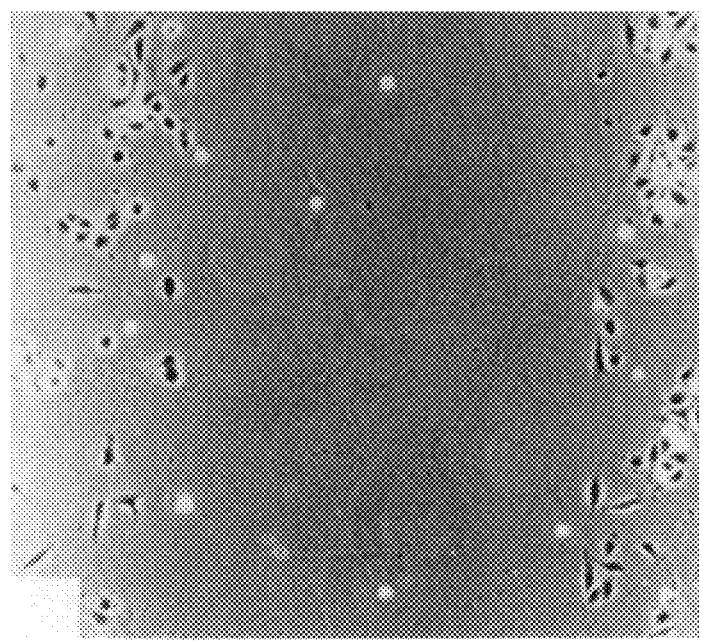
Figure 3B:
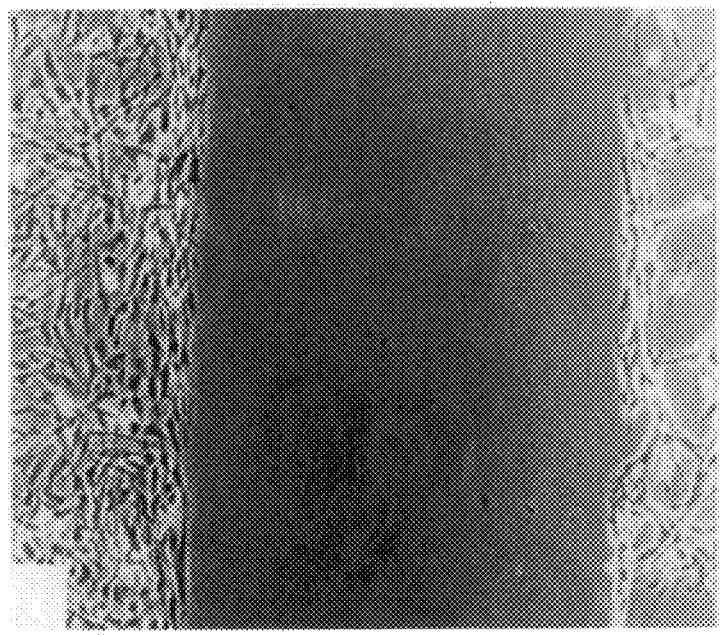
Figure 3C:
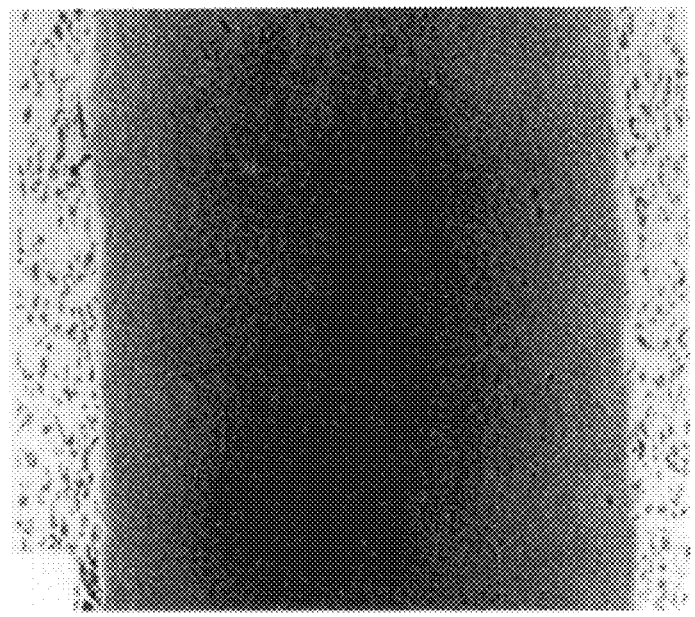
Figure 3D:
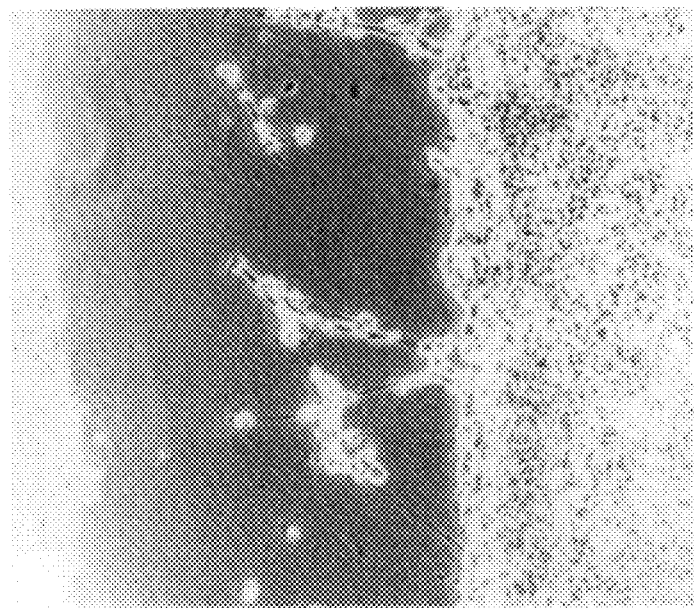

The stability of the inhibitory effect of DS-PG on C6 cells was followed for up to 6 days (FIG. 3) and that of 3T3 cells for up to 7 days (Table 7). The alternating clear stripes formed between confluent layers of cells at 0.8 mg/ml DS-PG were stable for at least 4 days (FIG. 3A–C). By 6 days small number of cells started to invade the DS-PG stripes (FIG. 3D). Similar results were obtained with 3T3 cells (Table 4).

TABLE 7

Time Dependent Effect of DS-PG on 3T3 Cell Migration

| Concentration (mg/ml) | 1 d | 2 d | 3 d | 4 d | 7 d |
|---|---|---|---|---|---|
| 0.8 (10 μM) | − | − | − | − | +/− |
| 0.4 (5 μM) | − | − | − | − | +/− |
| 0.2 (2.5 μM) | +/− | +/− | +/− | +/− | + |
| 0.1 (1.25 μM) | + | + | + | + | + |

The inhibitory effect at 0.8 and 0.4 mg/ml DS-PG was stable for at least 4 days; by day 7, only slight invasion was evident. Similarly, the slight inhibition at 0.2 mg/ml DS-PG was overcome by day 7. At 0.1 mg/ml DS-PG no inhibition was observed initially and the lack of inhibition persisted for at least 7 days.

In addition to primary cell cultures of fibroblasts and astrocytes, the effect of DS-PG was tested on fibroblasts and Schwann cells migrating from explant cultures of DRGS. Embryonic (E-8) chick DRGs were plated on alternating DS-PG/LN and LN stripes as described supra. At 0.8 mg/ml DS-PG/20 μg/ml LN, only a few DRGs attached to the LN substratum and demonstrated limited neurite outgrowth and non-neuronal cell migration (FIG. 4A). At 0.4 mg/ml DS-PG, DRGs attached to the LN substratum and expressed both neurite outgrowth and non-neuronal cell migration (FIG. 4B). At the interface between LN and DS-PG/LN stripes, elongating neurites and migrating non-neuronal cells either stopped abruptly or turned and travelled along the LN and DS-PG/LN stripe border. The inhibition by DS-PG was dose dependent, with lower concentrations (0.2 mg/ml) producing limited cell invasion. No inhibition of neurite and non-neuronal cell invasion was observed at 0.1 mg/ml DS-PG (Table 6).

7.2.2. Effect of KS/CS-PG on Cell Adhesion, Migration and Invasion

KS/CS-PG was tested for its effect on adhesion, migration and/or invasion of fibroblast and glial cell primary cultures and cell lines. Cell types tested included rat meningeal fibroblasts (RMF), adult rat sciatic nerve fibroblast (RSF), rat astrocytes (RAST), 3T3-mouse fibroblast cell line, C6-rat glioma cell line, and MCG-28 young immortalized mouse astrocytes. The cells were seeded in culture plates prepared as described in Section 7.1.2., supra, and evaluated for cell adhesion, migration and invasion.

Substratum containing a mixture of 2.7 mg/ml KS/CS-PG and 20 μg/ml LN inhibited the adhesion and migration of all cell types tested. Rat meningeal fibroblasts, 3T3 cells, rat astrocytes and chick DRG neurites were the most sensitive to KS/CS-PG inhibition (Table 8). Dose-response evaluation indicates that DRG neurons are the most sensitive cells to KS/CS-PG inhibition and the glial cell lines C6 and MCG-28 are the least sensitive. The initial inhibition of C6 cell adhesion (FIG. 5A), and later partial inhibition of cell migration and invasion observed at 2.7 mg/ml KS/CS-PG (FIG. 4B) was short lived. By 48 hr following plating, C6 overcame KS/CS-PG inhibition (FIG. 5C) and no banding was evident by 72 hr at the tested cell density.

TABLE 8

Effect of KS/CS-PG on Cell Migration

| Dose (mg/ml) | RMF | RSF | 3T3 | RAST | C6 | MCG28 | DRG |
|---|---|---|---|---|---|---|---|
| 2.7 | − | +/− | − | − | +/− | +/− | − |
| 1.0 | +/− | +/− | +/− | +/− | + | + | − |
| 0.5 | +/− | +/− | +/− | +/− | + | + | − |
| 0.25 | +/− | + | + | +/− | + | + | + |
| 0.12 | + | | | + | | | |

7.2.3. Comparison of DS-PG and KS-/CS-PG Activity

The data thus appear to indicate that DS-PG is a more potent inhibitor of cell adhesion, migration and invasion than KS/CS-PG (Table 6 vs. Table 8). This difference in potency is evident when the two proteoglycans are compared based on similar dry weight/volume (mg/ml) concentration. However, the estimated molecular weight of DS-PG is approximately 10 fold less than that of KS/CS-PG. When corrected for molar concentration, the differences in potency between DS-PG and KS/CS-PG is greatly reduced. For example, the estimated molar concentration of the KS/CS-PG at 1.0 mg/ml is 1.25 μM. DS-PG at the same molar concentration (1.25 μM 0.1 mg/ml) is no longer inhibitory, reflecting the results seen with KS/CS-PG (compare Tables 6 and 8).

7.2.4. Effect of Heparin and Dextran Sulfate on Cell Migration

Figure 6A:
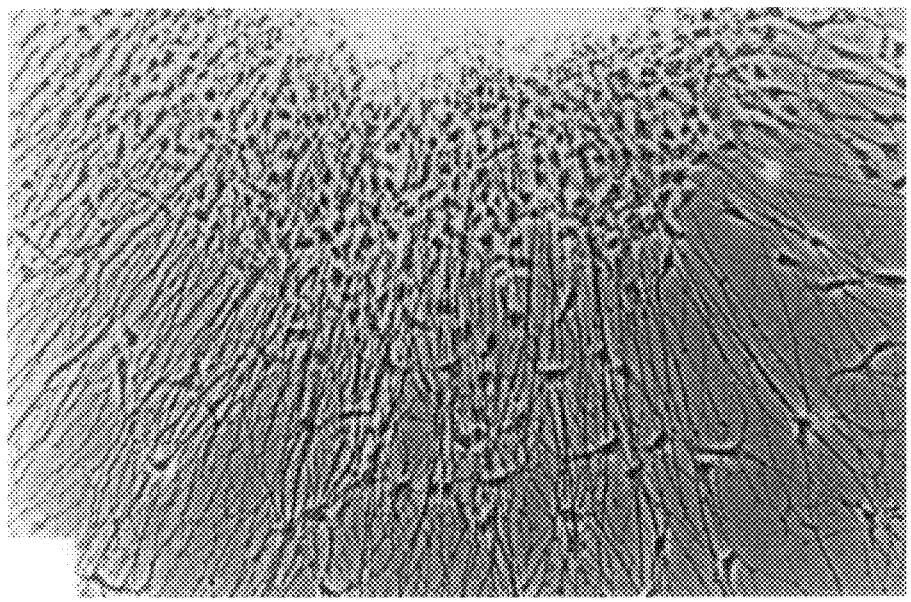
Figure 6B:
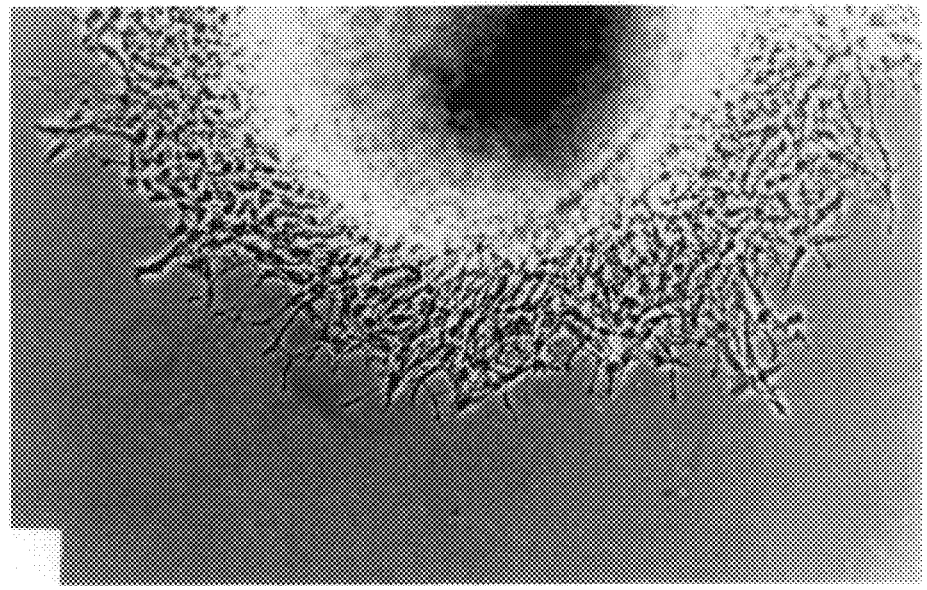
Figure 6C:
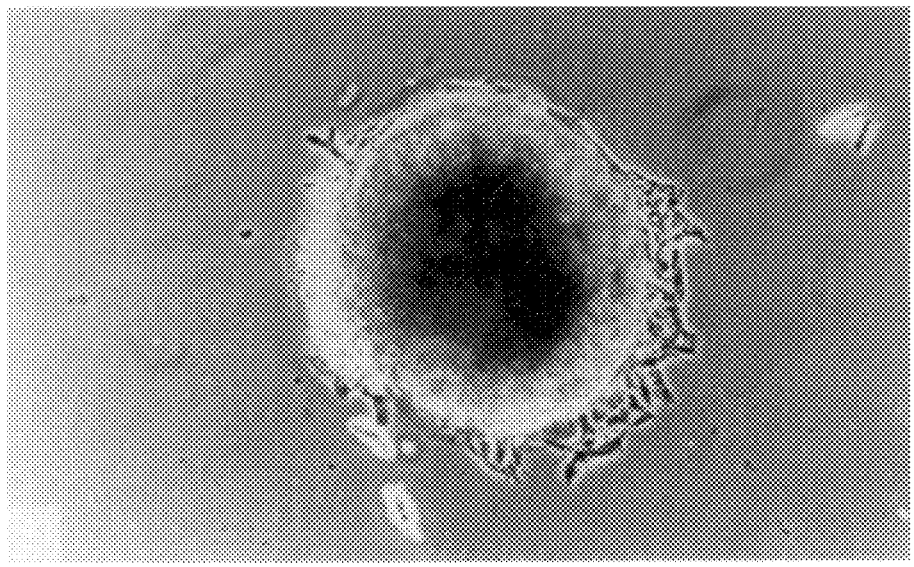
Figure 6D:
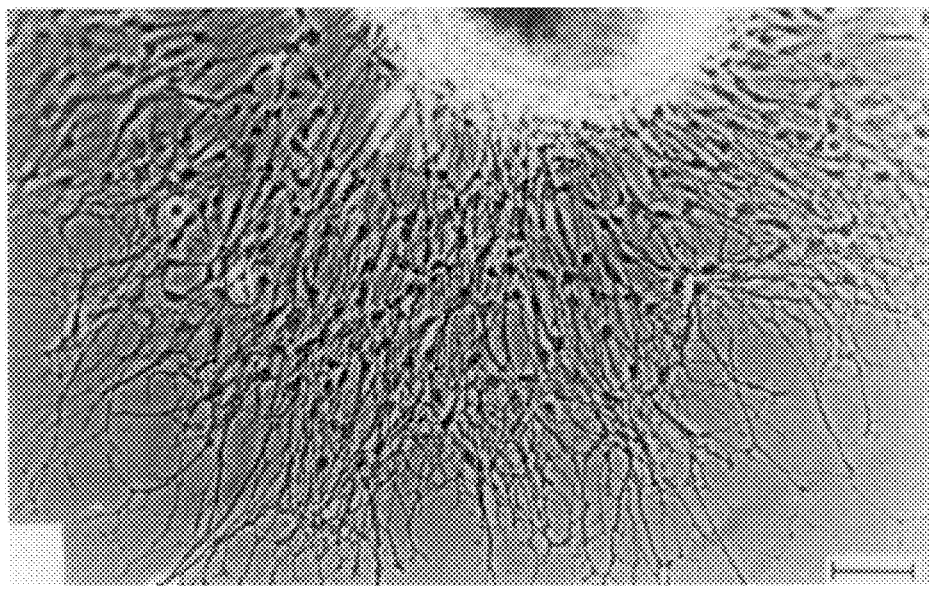

The effect of heparin and dextran sulfate on cell migration from explant cultures of chick DRGs was tested. DRGs were plated in culture dishes precoated with a substratum of either PLL or LN and grown in culture medium containing different concentrations of heparin, dextran sulfate or dextran solutions. In the absence of a test compound, within 24–48 hours a halo of neuritic outgrowth and migrating non-neuronal cells, i.e., fibroblasts and Schwann cells, was evident around the ganglia (FIG. 6A). The size of the cellular halo migrating from the DRG explant was reduced when the explant was grown in the presence of 0.4 mg/ml heparin (FIG. 6B). When the explant was grown in the presence of 0.2 mg/ml dextran sulfate, the size of the cellular halo around the DRG explant was dramatically reduced (FIG. 6C). In contrast, 0.4 mg/ml dextran had no effect (FIG. 6D). The size of the cellular halo emanating from DRGs grown in the presence of test compounds was evaluated relative to untreated control and rated as described in Section 8.1.3, supra (Table 9).

TABLE 9

Heparin and Dextran Sulfate Inhibit Cellular Migration from DRG Explants

| Concentration | Heparin | | Dextran Sul. | | Dextran | |
|---|---|---|---|---|---|---|
| (μg/ml) | LN | PLL | LN | PLL | LN | PLL |
| 400 | 5 | 1 | 1 | 1 | 5 | 5 |
| 200 | 5 | 2 | 1 | 1 | 5 | 5 |
| 50 | 5 | 2 | 1 | 1 | 5 | 5 |
| 10 | 5 | 2 | 1 | 1 | 5 | |
| 2 | | 2 | 3 | 1 | 5 | |
| 1.25 | 5 | 2 | 5 | 2 | | |

TABLE 9-continued

Heparin and Dextran Sulfate Inhibit
Cellular Migration from DRG Explants

| Concentration | Heparin | | Dextran Sul. | | Dextran | |
|---|---|---|---|---|---|---|
| (μg/ml) | LN | PLL | LN | PLL | LN | PLL |
| 1 | | 4 | | 3 | | |
| 0.5 | | 5 | | 5 | | |

Rating Scale (see Section 8.1.3., supra)
1 = 0–19%
2 = 20–39%
3 = 40–59%
4 = 60–79%
5 = 80–100% of control The effect of heparin and dextran sulfate was tested on two different substrata, LN and PLL. Both substrata support explant attachment, neurite outgrowth and non-neuronal cell migration from the explant. The two substrata differ in the mechanism by which cells adhere to them and the strength of that attachment. Attachment of cells to LN is thought to be a receptor mediated event, while PLL, a polycationic polymer, acts through ionic interactions. Cells display differential preference to either LN or PLL. In the case of DRG, the more adhesive substrata is LN. As shown in Table 9, heparin inhibited cell migration from DRG when grown on PLL but not on LN. This indicates a weaker inhibitory activity than that displayed by dextran sulfate, which is inhibitory even when DRGs are grown on LN. Heparin was weakly inhibitory at 1 μg/ml on PLL. Dextran sulfate was a stronger inhibitor at 1 μg/ml on PLL and at 2 μg/ml on LN. No inhibition of cell migration was observed with dextran when DRG is grown on either PLL or LN.

7.2.5. Inhibition of Fibroblast Adhesion Gags and Other Sulfated Carbohydrates

Since GAGs and other sulfated carbohydrates do not readily absorb to tissue culture plastic or other substrata, we adopted a quantitative assay to test their activity in solution. The adhesion of fibroblasts to PLL-coated microtiter plates in the presence of test compounds in the culture medium was evaluated using an MTT assay as described in section 8.1.5., supra, and the number of attached cells was expressed as percent of control. The effect of 4 hr incubation in the presence of heparin, pentosan polysulfate, dextran sulfate, and dextran on adhesion of rat meningeal fibroplasts (RMF) and 3T3 cells to PLL is shown in FIG. 7.

Heparin, pentosan polysulfate and dextran sulfate decreased the number of attached cells compared to untreated controls, while dextran treatment resulted in a slight increase in adherent cell number. The rank order of potency was similar when tested on either primary rat meningeal fibroblasts or the fibroblast cell line, 3T3. Adhesion of primary fibroblasts was inhibited by heparin, pentosan polysulfate and dextran sulfate more strongly than the 3T3 cell line. The effect of dextran and dextran sulfate on the number of attached cells 24 hours following treatment is shown in FIG. 8.

7.2.6. Effect of Gags and Other Polyanionic Compounds on Cell Migration

The effect of GAGs and other polyanionic molecules on cell adhesion and migration was tested using the simple and rapid model system of PC12 cell neurite outgrowth. PC12 cells grown in the presence of NGF extend neurites. The growth cone at the tip of the neurites mediates outgrowth through repeated cycles of attachment, detachment and migration. The net result of this process is neurite extension.

PC-12 cells primed with NGF were plated in 96-well plates. Test solutions were added to the wells and the cells were scored 2 days later as (+) if neurites of at least two cell bodies diameter in length were present on the majority of the cells, and (−) if no or only short processes were present. Complete dose-response curves were generated for each test compound and the results were expressed as $IC_{100}$ (g/ml), i.e., the minimum concentration at which the compound caused 100% inhibition of neurite outgrowth (Table 10). The lack of toxicity by each compound tested was confirmed as follows: microscopically, no evidence of cell death and detachment was seen; cells did not stain positive for trypan blue; and removal of the inhibitory compound from the culture medium resulted in neurite outgrowth. The compounds tested included GAGs (heparin, dermatan sulfate, chondroitin sulfate A, keratan sulfate and hyaluronic acid), sulfated carbohydrate polymers (dextran sulfate and pentosan polysulfate), and another polyanionic polymer (e.g., alginic acid).

TABLE 10

CORRELATION OF CELL MIGRATION INHIBITION
AND SULFUR CONTENT

| GAG | $IC_{100}$ (g/ml) | Sulfur Content |
|---|---|---|
| Heparin | $2.6 \times 10^{-7}$ | 11.8% |
| Pentosan Polysulfate | $3.9 \times 10^{-7}$ | 16.5% |
| Dextran sulfate | $5.2 \times 10^{-7}$ | 15.3% |
| Alginate | $3.1 \times 10^{-6}$ | 0% (COO⁻, no sulfur) |
| Dermatan sulfate 90% | $1.5 \times 10^{-5}$ | 6.0% |
| Hyaluronic acid | $2.0 \times 10^{-4}$ | 0.6–0.8% |
| Chondroitin sulfate A (porcine) | $5.0 \times 10^{-4}$ | 5.6% |
| Keratan sulfate | $>2.0 \times 10^{4}$ | 6.4% |
| Dextran | $>1.0 \times 10^{-3}$ | 0% |

A compound's relative inhibitory potency in vitro appeared to positively correlate with sulfur content. The contribution of the sulfur functional group is most clearly demonstrated by comparing the activity of dextran sulfate to that of dextran. The sulfur found as sulfate on the GAGs most likely affects cell invasion by anionic charge density. To test this hypothesis, we used alginic acid (alginate), a polyanionic polymer with a negative charge due only to carboxyl groups. As shown in Table 10, alginic acid also inhibits cell migration. These results indicate that an active inhibitory element of a given polymer is its anionic (negative) charge density.

7.2.7. Effect of Dextran Sulfate Molecular Size on Fibroblast Adhesion

Sulfated dextrans of similar sulfur content (15–16% by weight) and varied molecular size were tested for their effect on fibroblast adhesion. Using the colorimetric cell adhesion assay described in section 8.1.5., supra, dose-response curves were generated for 3T3 cells grown for 24 hrs in the presence of 5 kD, 8 kD, 500 kD and 2,000 kD dextran sulfate (FIG. 9). Inhibitory effect on 3T3 cell adhesion was observed with 5 kD, 8 kD, 500 kD and 2,000 kD dextran sulfate, but potency differed significantly. The $EC_{50}$ values for dextran sulfate inhibition of 3T3 cells adhesion were: 5 kD—6 mg/ml; 8 kD—4 mg/ml; 500 kD—0.006 mg/ml; and 2,000 kD—20 mg/ml. The most potent molecule in this assay is 500 kD dextran sulfate.

7.3. Conclusions

Scar formation and fibrosis result from uncontrolled invasion of fibroblasts to the site of an injury or lesion. Other detrimental conditions also result from uncontrolled cell invasion, such as neurite outgrowth, glial cell invasion, and monocyte/macrophage invasion. Inhibition of fibroblast invasion would prevent scarring and associated detrimental effects, such as surgical adhesions, e.g., peridural fibrosis, and cosmetically inappropriate scars, e.g., following cosmetic or reconstructive surgery. The foregoing results indicate that glycosaminoglycans and other anionic polymers inhibit invasion of fibroblasts, as well as other non-neuronal cells such as glial cells, and neurite outgrowth, and thus prevent associated detrimental effects.

The foregoing results also indicate that extent of inhibition correlates with anionic charge density, and that this relationship may be useful in predicting or identifying anionic polymers for use in the practice of the present invention. However, the in vivo results show that charge density only in part determines inhibitory potential.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference, in their entireties.

What is claimed is:

1. A method of inhibiting monocyte or macrophage invasion comprising administering to a site in a mammal where inhibition of monocyte or macrophage invasion is desired, a composition comprising an amount effective to inhibit monocyte or macrophage invasion, of a composition comprising an anionic polymer.

2. The method according to claim 1 in which the anionic polymer is selected from the group consisting of dermatan sulfate, chondroitin sulfate, keratan sulfate, heparan sulfate, heparin, dextran sulfate, pentosan polysulfate, alginate, and hyaluronic acid.

3. The method according to claim 1 in which the anionic polymer comprises an acid sulfate and has a sulfur content greater than 5%.

4. The method according to claim 3 in which the anionic polymer is selected from the group consisting of dermatan sulfate, chondroitin sulfate, keratan sulfate, heparan sulfate, heparin, dextran sulfate, pentosan polysulfate, and hyaluronic acid.

5. The method according to claim 3 in which the sulfur content of the anionic polymer is greater than 10%.

6. A method for inhibiting monocyte or macrophage invasion comprising administering to a site in a mammal where inhibition of monocyte or macrophage invasion is desired, a composition comprising an amount effective to inhibit monocyte or macrophage invasion, said composition comprising dextran sulfate.

7. The method according to claim 6 in which the sulfur content of the dextran sulfate is greater than 10% by weight.

8. The method according to claim 6 in which the average molecular weight of the dextran sulfate is in the range of 40,000 to 500,000 Daltons.

9. A method for inhibiting monocyte or macrophage invasion comprising administering to a site in a mammal where inhibition of monocyte or macrophage invasion is desired, (a) an amount of a composition comprising an anionic polymer effective to inhibit monocyte or macrophage invasion; and (b) an amount of an adhesive protein effective to anchor the anionic polymer at the site where inhibition of monocyte or macrophage invasion is desired.

10. The method according to claim 9 in which the anionic polymer is selected from the group consisting of dermatan sulfate, chondroitin sulfate, keratan sulfate, heparan sulfate, heparin, dextran sulfate, pentosan polysulfate, alginate, and hyaluronic acid.

11. The method according to claim 9 in which the anionic polymer comprises an acid sulfate and has a sulfur content greater than 5%.

12. The method according to claim 11 in which the anionic polymer is selected from the group consisting of dermatan sulfate, chondroitin sulfate, keratan sulfate, heparan sulfate, heparin, dextran sulfate, pentosan polysulfate, and hyaluronic acid.

13. The method according to claim 11 in which the sulfur content of the anionic polymer is greater than 10%.

14. A method for inhibiting monocyte or macrophage invasion comprising administering to a site in a mammal where inhibition of monocyte or macrophage invasion is desired, (a) an amount of dextran sulfate effective to inhibit monocyte or macrophage invasion; and (b) an amount of an adhesive protein effective to anchor the dextran sulfate at the site where inhibition of monocyte or macrophage invasion is desired.

15. The method according to claim 14 in which the sulfur content of the dextran sulfate is greater than 10% by weight.

16. The method according to claim 14 in which the average molecular weight of the dextran sulfate is in the range of 40,000 to 500,000 Daltons.

17. The method according to claim 1, In which the site is a lesion.

18. The method according to claim 9, in which the site is a lesion.

19. The method according to claim 17 or 18 in which the anionic polymer is selected from the group consisting of dermatan sulfate, chondroitin sulfate, keratan sulfate, heparan sulfate, heparin, dextran sulfate, pentosan polysulfate, alginate, and hyaluronic acid.

20. The method according to claim 17 or 18 in which the anionic polymer comprises an acid sulfate and has a sulfur content greater than 5%.

21. The method according to of claim 19 in which the anionic polymer is selected from the group consisting of dermatan sulfate, chondroitin sulfate, keratan sulfate, heparan sulfate, heparin, dextran sulfate, pentosan polysulfate, and hyaluronic acid.

22. The method according to claim 17 or 18 in which the anionic polymer is dextran sulfate.

23. The method according to claim 22 in which the sulfur content of the dextran sulfate is greater than 10% by weight.

24. The method according to claim 22 in which the average molecular weight of the dextran sulfate is in the range of 40,000 to 500,000 Daltons.

25. The method according to claim 17 or 18 in which the monocyte or macrophage invasion is caused by a disease or disorder selected from the group consisting of trauma, surgery, viral infection, bacterial infection, metabolic disease, malignancy, exposure to toxic agents, and hyperplastic situations.

26. The method according to claim 17 or 18 in which the lesion is a surgical lesion.

27. The method according to claim 17 or 18 in which the lesion results from a traumatic injury.

28. The method according to claim 9, 14, or 18 in which the adhesive protein is selected from the group consisting of fibrin, mussel polyphenolic adhesion protein, barnacle polyphenolic adhesion protein, oyster polyphenolic adhesion protein, chemically polymerized peptide from an adhesion protein, and a recombinantly produced analog adhesion protein.

29. The method according to claim 26 in which the surgical lesion results from a laminectomy, fallopian tube surgery, plastic surgery or surgery to treat temporomandibular joint dysfunction.

30. The method according to claim 26 in which the surgical lesion results from abdominal surgery, joint surgery, tendon surgery, surgery to remove pelvic sidewall adhesions, peritoneal surgery, thoracic surgery, vascular surgery, cardiac surgery, heart bypass surgery, heart valve replacement surgery, or open heart surgery.

31. A method of inhibiting monocyte or macrophage invasion in a mammal following laminectomy, comprising administering a composition comprising an amount effective to inhibit monocyte or macrophage invasion, of an anionic polymer to a laminectomy site in a mammal.

32. The method according to claim 31 in which the anionic polymer is selected from the group consisting of dermatan sulfate, chondroitin sulfate, keratan sulfate, heparan sulfate, heparin, dextran sulfate, pentosan polysulfate, alginate, and hyaluronic acid.

33. The method according to claim 31 in which the anionic polymer comprises an acid sulfate and has a sulfur content greater than 5%.

34. The method according to claim 33 in which the anionic polymer is selected from the group consisting of dermatan sulfate, chondroitin sulfate, keratan sulfate, heparan sulfate, heparin, dextran sulfate, pentosan polysulfate, and hyaluronic acid.

35. The method according to claim 33 in which the sulfur content of the anionic polymer is greater than 10%.

36. A method of inhibiting monocyte or macrophage invasion in a mammal following laminectomy, comprising administering a composition comprising an amount effective to inhibit monocyte or macrophage invasion, of dextran sulfate to a laminectomy site in a mammal.

37. The method according to claim 36 in which the sulfur content of the dextran sulfate is greater than 10% by weight.

38. The method according to claim 36 in which the average molecular weight of the dextran sulfate is in the range of 40,000 to 500,000 Daltons.

39. The method according to claim 31 or 36 in which the composition further comprises a semi-solid pharmaceutically acceptable carrier.

40. A method of inhibiting monocyte or macrophage invasion around an implant in a mammal comprising applying a composition comprising an amount effective to inhibit monocyte or macrophage invasion, of an anionic polymer to an implant; and administering the implant to a mammal.

41. The method according to claim 40 in which the anionic polymer is selected from the group consisting of dermatan sulfate, chondroitin sulfate, heparan sulfate, heparin, dextran sulfate, pentosan polysulfate, alginate, and hyaluronic acid.

42. The method according to claim 40 in which the anionic polymer comprises an acid sulfate and has a sulfur content greater than 5%.

43. The method according to claim 42 in which the anionic polymer is selected from the group consisting of dermatan sulfate, chondroitin sulfate, keratan sulfate, heparan sulfate, heparin, dextran sulfate, pentosan polysulfate, and hyaluronic acid.

44. The method according to claim 42 in which the sulfur content of the anionic polymer is greater than 10%.

45. A method of inhibiting monocyte or macrophage invasion around an implant in a mammal comprising applying a composition comprising an amount of dextran sulfate effective to inhibit monocyte or macrophage invasion, to an implant and administering the implant to a mammal.

46. The method according to claim 45 in which the sulfur content of the dextran sulfate is greater than 10% by weight.

47. The method according to claim 45 in which the average molecular weight of the dextran sulfate is in the range of 40,000 to 500,000 Daltons.

48. The method according to claim 45 in which the implant is selected from the group consisting of intravenous catheter, nephrostomy tube, peritoneal drainage tube, artificial hip joint, artificial heart valve, and peripheral nerve repair, and other prostheses.

* * * * *